US012644144B2

(12) United States Patent
Urano et al.

(10) Patent No.: US 12,644,144 B2
(45) Date of Patent: Jun. 2, 2026

(54) FLUORESCENT PROBE FOR DETECTION OF ENPP ACTIVITY

(71) Applicants: THE UNIVERSITY OF TOKYO, Tokyo (JP); PUBLIC UNIVERSITY CORPORATION NAGOYA CITY UNIVERSITY, Aichi (JP); RIKEN, Saitama (JP)

(72) Inventors: Yasuteru Urano, Tokyo (JP); Toru Komatsu, Tokyo (JP); Shingo Sakamoto, Tokyo (JP); Hiroyuki Noji, Tokyo (JP); Hidehiko Nakagawa, Aichi (JP); Mitsuyasu Kawaguchi, Aichi (JP); Rikiya Watanabe, Saitama (JP)

(73) Assignees: THE UNIVERSITY OF TOKYO, Tokyo (JP); PUBLIC UNIVERSITY CORPORATION NAGOYA CITY UNIVERSITY, Aichi (JP); RIKEN, Saitama (JP)

( * ) Notice: Subject to any disclaimer, the term of this patent is extended or adjusted under 35 U.S.C. 154(b) by 1191 days.

(21) Appl. No.: 17/616,784

(22) PCT Filed: Jun. 8, 2020

(86) PCT No.: PCT/JP2020/022546

§ 371 (c)(1),
(2) Date: Feb. 10, 2022

(87) PCT Pub. No.: WO2020/246616

PCT Pub. Date: Dec. 10, 2020

(65) Prior Publication Data

US 2023/0052551 A1 Feb. 16, 2023

Related U.S. Application Data

(60) Provisional application No. 62/858,388, filed on Jun. 7, 2019.

(51) Int. Cl.
*C12Q 1/44* (2006.01)
*G01N 21/64* (2006.01)

(52) U.S. Cl.
CPC .......... *C12Q 1/44* (2013.01); *G01N 21/6428* (2013.01); *G01N 21/6458* (2013.01)

(58) Field of Classification Search
CPC .......... C07H 19/10; C07H 19/20; C12Q 1/42; C12Q 1/44; C09B 11/06
See application file for complete search history.

(56) References Cited

U.S. PATENT DOCUMENTS

| | | | | |
|---|---|---|---|---|
| 2008/0014602 A1* | 1/2008 | Nagano | C09B 11/08 435/18 |
| 2014/0272990 A1 | 9/2014 | Zhou et al. | |

FOREIGN PATENT DOCUMENTS

| | | |
|---|---|---|
| JP | 2016-512042 | 4/2016 |
| WO | 2010/126075 | 11/2010 |
| WO | 2018/159810 | 9/2018 |

OTHER PUBLICATIONS

Kawaguchi et al., "Development of ENPPI activity detected fluorescence probes and chemical screening", Lecture abstracts of the Medicinal Chemistry Symposium, vol. 35th, 2017, pp. 98.
Kawaguchi et al., "Screening and X-ray Crystal Structure-based Optimization of Autotaxin (ENPP2) Inhibitors, Using a Newly Developed fluorescence Probe", ACS Chemical Biology, 2013, vol. 8, No. 8, pp. 1713-1721.
Kawaguchi et al., "fluorescence Probe for Lysophospholipase C/NPP6 Activity and a Potent NPP6 Inhibitor", Journal of the American Chemical Society, 2011, vol. 133, No. 31, pp. 12021-12030.
International Search Report issued in International Patent Application No. PCT/JP2020/022546, dated Aug. 18, 2020, along with an English translation thereof.
Extended European Search Report issued in EP Patent Application No. 20818992.8, Jun. 16, 2023.
Kawaguchi et al., "Development of an ENPP1 Fluorescence Probe for Inhibitor Screening, Cellular Imaging, and Prognostic Assessment of Malignant Breast Cancer", Journal of Medicinal Chemistry, vol. 62, No. 20, Sep. 19, 2019, pp. 9254-9269.

* cited by examiner

*Primary Examiner* — Pancham Bakshi
(74) *Attorney, Agent, or Firm* — Greenblum & Bernstein, P.L.C.

(57) ABSTRACT

Provided is a novel fluorescent probe.
A compound of the following general formula (I) or a salt thereof.

(I)

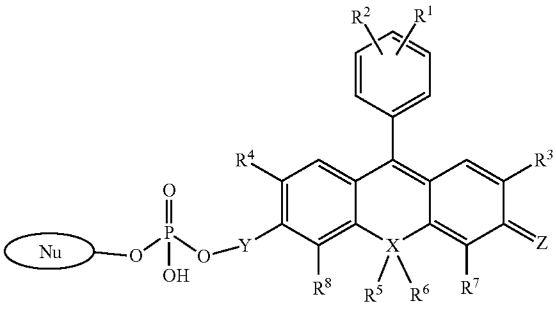

9 Claims, 10 Drawing Sheets

FLUORESCENT PROBE FOR DETECTION OF ENPP ACTIVITY

TECHNICAL FIELD

The present invention relates to a fluorescent probe for detecting ENPP, and use thereof. Specifically, the present invention relates to a compound, a fluorescent probe for detecting ENPP, a microdevice, and a method for detecting the enzyme activity of ENPP in a biological sample.

BACKGROUND ART

Methods for detecting enzyme activity at a single enzyme level using a microdevice have been generally used for the purpose of, for example, clarifying individual biochemical parameters of enzymes, and detecting the presence of a specific protein with good sensitivity using the enzyme as a reporter protein.

Further, by applying a recently developed microdevice-compatible phosphatase activity detection fluorescent probe (Patent Literature 1), a plurality of phosphatases in a biological sample have been isolated and detected to successfully find a difference between a healthy person and a patient with a disease, and development to establishment of a new method for diagnosis of pathologic conditions.

However, existing phosphatase activity detection fluorescent probes have a problem of having limited performance regarding the purpose of finding a new disease biomarker because the structure of an enzyme recognition site is a phosphoric acid monoester, and thus the types of enzymes capable of detecting activity are limited.

On the other hand, ENPP (Ectonucleotide pyrophosphatase/phosphodiesterase family) is an enzyme which hydrolyzes a substrate such as extracellular nucleotide triphosphate, and the presence of seven subtypes has been confirmed. Some of these subtypes have been reported to be associated with diseases like ENPP2 known as Autotaxin, but many of them have unknown functions.

Heretofore, there have not been reported cases where the activity of the subtypes other than ENPP2 was detected in the blood, and if the activity of a very small amount of ENPP that may be present in a biological sample can be newly detected, the detection is expected to lead to discovery of a new biomarker.

CITATION LIST

Patent Literature

Patent Literature 1: WO 2018/159810 A1

SUMMARY OF INVENTION

Technical Problem to Be Solved by the Invention

The present invention provides a novel fluorescent probe and an intermediate thereof. More specifically, an object of the present invention is to provide a fluorescent probe for detecting ENPP.

Means for Solving Problem

For solving the above-described problems, the present inventors have studied to design a novel fluorescent probe in which a structure that can be a new enzyme substrate is introduced to a phosphoric acid monoester site that is an enzyme recognition site in a conventional microdevice-compatible fluorescent probe. As a result, the present inventors have found that such a fluorescent probe is metabolized to ENPP having a nucleic acid as a substrate, and cause an increase in fluorescence intensity, leading to completion of the present invention.

Specifically, the present invention provides the following.

[1] A compound of the following general formula (I) or a salt thereof:

(I)

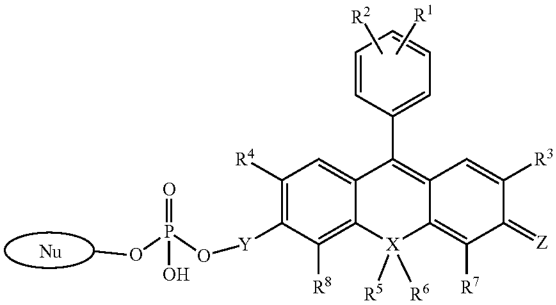

wherein $R^1$ is one or two monovalent substituents present on a benzene ring, which are electron donating groups, and when a plurality of $R^1$s are present, $R^1$s are the same or different;

$R^2$ is one or two monovalent substituents present on a benzene ring, which have an anionic functional group at an end, and when a plurality of $R^2$s are present, $R^2$s are the same or different;

$R^3$ and $R^4$ are each independently a hydrogen atom, an alkyl group having 1 to 6 carbon atoms, or a halogen atom;

$R^5$ and $R^6$ are each independently an alkyl group having 1 to 6 carbon atoms, or an aryl group;

$R^7$ and $R^9$ are each independently a hydrogen atom, an alkyl group having 1 to 6 carbon atoms, or a halogen atom;

X is a silicon atom, a phosphorus atom, a germanium atom or a tin atom;

Z is an oxygen atom or $N^+R^9R^{10}$, where $R^9$ and $R^{10}$ are each independently a hydrogen atom, or an alkyl group having 1 to 10 carbon atoms, $R^9$ and $R^{10}$ are optionally linked together to form a four- to seven-membered heterocyclyl containing a nitrogen atom bonded to $R^9$ and $R^{10}$, and $R^9$ or $R^{10}$, or each of both $R^9$ and $R^{10}$ is optionally linked with $R^3$ or $R^7$ to form a five- to seven-membered heterocyclyl or heteroaryl containing a nitrogen atom bonded to $R^5$ or $R^{10}$, or optionally contains one to three additional hetero atoms selected from the group consisting of an oxygen atom, a nitrogen atom and a sulfur atom as ring forming members, and the heterocyclyl or heteroaryl is optionally substituted with an alkyl having 1 to 6 carbon atoms, an alkenyl having 2 to 6 carbon atoms, an alkynyl having 2 to 6 carbon atoms, an aralkyl group having 6 to 10 carbon atoms, or an alkyl-substituted alkenyl group having 6 to 10 carbon atoms;

Y is a single bond, $-O-(CH_2)_{a1}-$, $-O-(CH_2)_{n2}-Ar_1-$, $-NH-(CH_2)_{n3}-$ or $-NH-(CH_2)_{n4}-Ar_2-$, where n1, n2, n3 and n4 are each independently an integer of 1 to 10, and $Ar_1$ and $Ar_2$ are each independently a substituted or unsubstituted arylene group; and

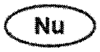

(Nu) is represented by R—S— where R is an organic base, and

S is a sugar or a partial structure of a derivative thereof, or a single bond.

[2] A compound of the following general formula (II) or a salt thereof:

(II)

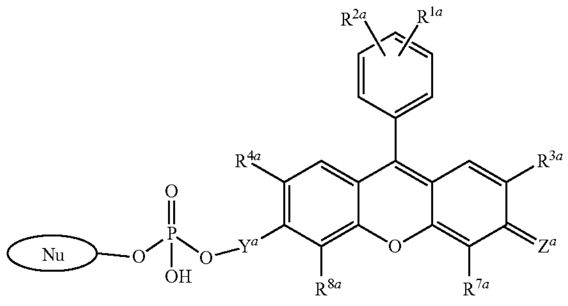

wherein $R^{1a}$ is one or two monovalent substituents present on a benzene ring, which are electron donating groups, and when a plurality of $R^{1a}$s are present, $R^{1a}$s are the same or different;

$R^{2a}$ is one or two monovalent substituents present on a benzene ring, which have an anionic functional group at an end, and when a plurality of $R^{2a}$s are present, $R^{2a}$s are the same or different;

$R^{3a}$ and $R^{4a}$ are each independently a hydrogen atom, an alkyl group having 1 to 6 carbon atoms, or a halogen atom;

$R^{5a}$ and $R^{6a}$ are each independently an alkyl group having 1 to 6 carbon atoms, or an aryl group;

$R^{7a}$ and $R^{3a}$ are each independently a hydrogen atom, an alkyl group having 1 to 6 carbon atoms, or a halogen atom;

$Z^a$ is an oxygen atom or $N^+R^{9a}R^{10a}$, where $R^{9a}$ and $R^{10a}$ are each independently a hydrogen atom, or an alkyl group having 1 to 10 carbon atoms, $R^{9a}$ and $R^{10a}$ are optionally linked together to form a four- to seven-membered heterocyclyl containing a nitrogen atom bonded to $R^{9a}$ and $R^{10a}$, and $R^{9a}$ or $R^{10a}$, or each of both $R^{9a}$ and $R^{10a}$ is optionally linked with $R^{3a}$ or $R^{10a}$ to form a five- to seven-membered heterocyclyl or heteroaryl containing a nitrogen atom bonded to $R^{9a}$ or $R^{10a}$, or optionally contains one to three additional hetero atoms selected from the group consisting of an oxygen atom, a nitrogen atom and a sulfur atom as ring forming members, and the heterocyclyl or heteroaryl is optionally substituted with an alkyl having 1 to 6 carbon atoms, an alkenyl having 2 to 6 carbon atoms, an alkynyl having 2 to 6 carbon atoms, an aralkyl group having 6 to 10 carbon atoms, or an alkyl-substituted alkenyl group having 6 to 10 carbon atoms;

$Y^a$ is a single bond, $—O—(CH_2)_{n1}—$, $—O—(CH_2)_{n2}—Ar_1—$, $—NH—(CH_2)_{n3}—$ or $—NH—(CH_2)_{n4}—Ar_2—$, where n1, n2, n3 and n4 are each independently an integer of 1 to 10, and $Ar_1$ and $Ar_2$ are each independently a substituted or unsubstituted arylene group; and

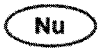

(Nu) is represented by R—S— where R is an organic base, and

S is a sugar or a partial structure of a derivative thereof, or a single bond.

[3] The compound according to [1] or [2] or a salt thereof, wherein the sugar of S or a derivative thereof is ribose, deoxyribose, or a derivative thereof.

[4] The compound according to any one of [1] to [3] or a salt thereof, wherein the organic base of R is selected from the group consisting of a nucleic acid base and a derivative thereof, $(CH_3)_3N^+—C_2H_4—$, $(CH_3CH_2)_2N—$ and $R_2N$ (R is a hydrogen atom, or an alkyl group having 1 to 10 carbon atoms, and Rs are the same or different).

[5] The compound according to [4] or a salt thereof, wherein the nucleic acid base is selected from the group consisting of adenine, thymine, cytosine, guanine and uracil.

[6] The compound according to any one of [1] to [5] or a salt thereof, wherein the anionic functional group is one selected from the group consisting of a carboxy group, a sulfonic acid group and a phosphoric acid group.

[7] The compound according to any one of [1] to [6], wherein $R^1$ is an alkoxy group having 1 to 10 carbon atoms.

[8] A fluorescent probe for detecting ENPP, comprising the compound according to any one of [1] to [7].

[9] A test kit for the enzyme activity of ENPP, comprising the compound according to any one of [1] to [7].

[10] A kit comprising the compound according to any one of [1] to [7] and a plate provided with microwells containing the compound.

[11] A method for measuring the enzyme activity of ENPP, including bringing ENPP into contact with the compound according to any one of [1] to [7].

[12] The method according to [11], wherein the contact is performed in the presence of serum.

[13] The kit according to [10], including two or more types of the fluorescent probes for detecting ENPP which have different reaction points in one well and different fluorescence wavelengths.

[14] A method for detecting the enzyme activity of ENPP3, comprising bringing ENPP3 into contact with the following compound (A) and/or the following compound (B).

(A)

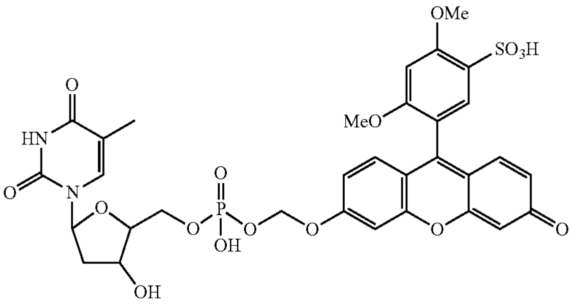

-continued (B)

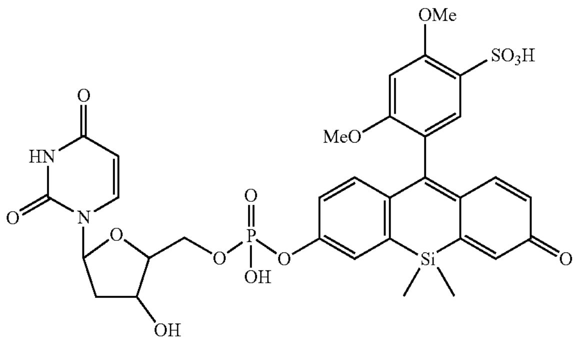

[15] The method according to [14], wherein the contact is a contact of ENPP3 with both the compound (A) and the compound (B).

Advantageous Effects of Invention

According to the present invention, it is possible to provide a fluorescent probe for detecting ENPP.

ENPP is known to have seven subtypes, but it has not been reported that the activity of the subtypes other than ENPP2 which is known as autotaxin was present in the blood, and association with diseases has been unknown for many of the subtypes. The fluorescent probe of the present invention enables measurement of the activity of ENPP in a biological sample (e.g. body fluid). The fluorescent probe of the present invention is advantageous in that physiological functions can be taken into consideration because evaluation can be made on the basis of the activity of ENPP rather than the amount of protein thereof. In addition, the fluorescent probe of the present invention is expected to newly detect the activity of a very small amount of ENPP that may be present in a biological sample, leading to discovery of a new biomarker.

DESCRIPTION OF EMBODIMENTS

Figure 1:
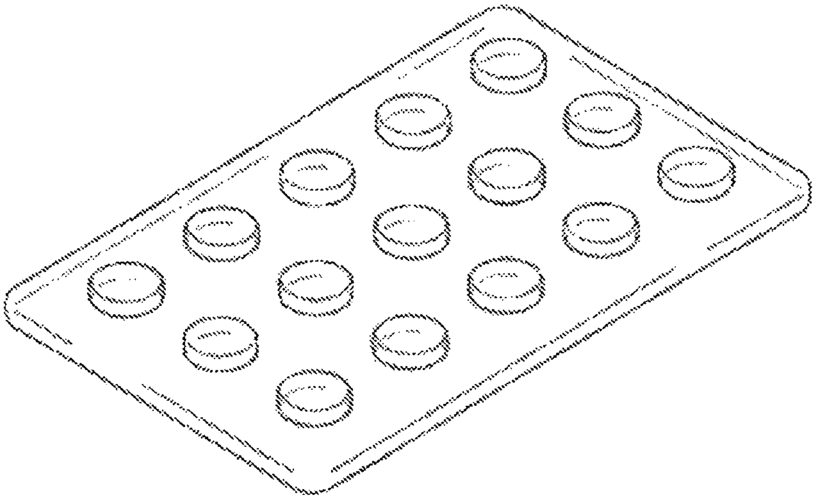
FIG. 1 is a perspective view schematically showing a microdevice according to an embodiment of the present invention.

Herein, the "halogen atom" means a fluorine atom, a chlorine atom, a bromine atom or an iodine atom.

Herein, the "alkyl" may be any of linear, branched and cyclic aliphatic hydrocarbon groups or combinations thereof. The number of carbon atoms in the alkyl group is not particularly limited, and is, for example, 1 to 6 ($C_{1-6}$), 1 to 10 ($C_{1-10}$), 1 to 15 ($C_{1-15}$), or 1 to 20 ($C_{1-20}$). A specified number of carbon atoms means an "alkyl" having the specified number of carbon atoms. For example, $C_{1-8}$ alkyls include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. Herein, the alkyl group may have one or more arbitrary substituents. Examples of the substituent include, but are not limited to, alkoxy groups, halogen atoms, amino groups, mono- or di-substituted amino groups, substituted silyl groups and acyl. When the alkyl group has two or more substituents, the substituents may be the same or different. The same applies to alkyl moieties of other substituents including alkyl moieties (e.g. alkoxy groups and arylalkyl groups).

Herein, when a certain functional group is defined as being "optionally substituted", the type of substituent, the substitution position and the number of substituents are not particularly limited, and two or more substituents are present, they may be the same or different. Examples of the substituent include but are not limited to, alkyl groups, alkoxy groups, hydroxyl groups, carboxyl groups, halogen atoms, sulfo groups, amino groups, alkoxycarbonyl groups and oxo groups. These substituents may further have substituents. Examples of such groups include, but are not limited to, halogenated alkyl groups and dialkylamino groups.

Herein, the "aryl" may be either a monocyclic aromatic hydrocarbon group or a condensed polycyclic aromatic hydrocarbon group, and may be an aromatic heterocyclic ring containing one or more hetero atoms (e.g. an oxygen atom, a nitrogen atom or a sulfur atom) as ring forming atoms. Here, the aromatic heterocyclic ring may also be referred to as "heteroaryl" or "heteroaromatic". The aryl may be attached at all possible positions, whether it is a monocyclic ring or a condensed ring. Non-limiting examples of the monocyclic aryl include a phenyl group (Ph), a thienyl group (2- or 3-thienyl group), a pyridyl group, a furyl group, a thiazolyl group, an oxazolyl group, a pyrazolyl group, a 2-pyrazinyl group, a pyrimidinyl group, a pyrrolyl group, an imidazolyl group, a pyridazinyl group, a 3-isothiazolyl group, a 3-isoxazolyl group, a 1,2,4-oxadiazol-5-yl group and a 1,2,4-oxadiazol-3-yl group. Non-limiting examples of the condensed polycyclic aryl include a 1-naphthyl group, a 2-naphthyl group, a 1-indenyl group, a 2-indenyl group, a 2,3-dihydroindene-1-yl group, a 2,3-dihydroindene-2-yl group, a 2-anthryl group, an indazolyl group, a quinolyl group, an isoquinolyl group, a 1,2-dihydroisoquinolyl group, a 1,2,3,4-tetrahydroisoquinolyl group, an indolyl group, an isoindolyl group, a phthalazinyl group, a quinoxalinyl group, a benzofuranyl group, a 2,3-dihydrobenzofuran-1-yl group, a 2,3-dihydrobenzofuran-2-yl group, a 2,3-dihydrobenzothiophene-1-yl group, a 2,3-dihydrobenzothiophene-2-yl group, a benzothiazolyl group, a benzimidazolyl group, a fluorenyl group and a thioxanthenyl group. Herein, the aryl group may have one or more arbitrary substituents on the ring thereof. Examples of the substituent include, but are not limited to, alkoxy groups, halogen atoms, amino groups, mono- or di-substituted amino groups, substituted silyl groups and acyl. When the aryl group has two or more substituents, the substituents may be the same or different. The same applies to aryl moieties of other substituents including aryl moieties (e.g. aryloxy groups and arylalkyl groups).

Herein, the "alkoxy group" is a structure in which the alkyl group is bonded to an oxygen atom, and examples thereof include saturated linear, branched and cyclic alkoxy groups or combinations thereof. Examples of suitable groups include a methoxy group, an ethoxy group, a n-propoxy group, an isopropoxy group, a cyclopropoxy group, a n-butoxy group, an isobutoxy group, a s-butoxy group, a t-butoxy group, a cyclobutoxy group, a cyclopropylmethoxy group, a n-pentyloxy group, a cyclopentyloxy group, a cyclopropylethyloxy group, a cyclobutylmethyloxy group, a n-hexyloxy group, a cyclohexyloxy group, a cyclopropylpropyloxy group, a cyclobutylethyloxy group and a cyclopentylmethyloxy group.

Herein, the "alkylene" is a divalent group composed of a linear or branched saturated hydrocarbon, and examples thereof include methylene, 1-methylmethylene, 1,1-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2 diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene and 2,2-di-n-propyltrimethylene.

1. Compound of General Formula (I) or Salt Thereof

An embodiment of the present invention is a compound of the following general formula (I) or a salt thereof.

(I)

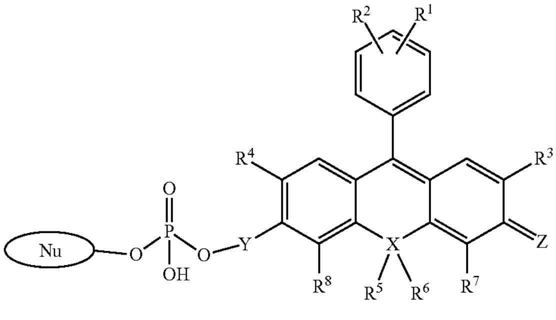

In the general formula (I), $R^1$ represents one or two monovalent substituents present on a benzene ring, which are electron donating groups.

When a plurality of $R^1$s are present, $R^1$s are the same or different.

The "electron donating group" herein may be a substituent capable donating an electron to a benzene ring. Specific examples thereof include, but are not limited to, a hydroxyl group, an alkoxy group having 1 to 10 carbon atoms, an amino group, and an alkylamino group having 1 to 10 carbon atoms. The number of $R^1$s is 1 or 2, preferably 2. If there are two $R^1$s, $R^1$s are the same or different. In particular, when there are two $R^1$s, it is preferable that $R^1$s are the same because of easy synthesis.

The alkoxy group having 1 to 10 carbon atoms in $R^1$ may have a structure in which a linear or branched alkyl group having 1 to 10 carbon atoms is bonded to an oxygen atom. Specific examples of the alkoxy group having 1 to 10 carbon atoms include a methoxy group, an ethoxy group, a n-propoxy group, an isopropoxy group, a n-butoxy group, an isobutoxy group, a sec-butoxy group, a tert-butoxy group, a n-pentoxy group, an isopentoxy group, a neopentoxy group, a tert-pentoxy group, a 1-methylbutoxy group, a n-hexitoxy group, a 2-methylpentoxy group, a 3-methylpentoxy group, a 2,2-dimethylbutoxy group, a 2,3-dimethylbutoxy group, a n-heptoxy group, a 2-methylhexitoxy group, a 3-methylhexitoxy group, a 2,2-dimethylpentoxy group, a 2,3-dimethylpentoxy group, a 2,4-dimethylpentoxy group, a 3,3-dimethylpentoxy group, a 3-ethylpentoxy group, a 2,2,3-trimethylbutoxy group, a n-octoxy group, an isooctoxy group, a 2-ethylhexitoxy group, a noninoxy group and a decyloxy group. In particular, the alkoxy group having 1 to 10 carbon atoms in $R^1$ is preferably a linear alkoxy group, more preferably a methoxy group or an ethoxy group.

The alkylamino group having 1 to 10 carbon atoms in $R^1$ may have a structure in which a linear or branched alkyl group having 1 to 10 carbon atoms is bonded to an amino group. Specific examples of the alkylamino group having 1 to 10 carbon atoms include a methylamino group, an ethylamino group, an isopropylamino group, a dimethylamino group, a diethylamino group and a diisopropylamino group. In particular, the alkylamino group having 1 to 10 carbon atoms in $R^1$ is preferably a linear alkylamino group, more preferably a methylamino group or an ethylamino group.

In particular, $R^1$ in the general formula (2) is preferably a linear alkoxy group having 1 to 10 carbon atoms or a linear alkylamino group having 1 to 10 carbon atoms, more preferably a methylamino group, an ethylamino group, a methoxy group or an ethoxy group, because of high hydrophilicity.

In addition, it is preferable that there are two $R^1$s in the general formula (1). It is preferable that the two $R^1$s on the benzene ring are located at an ortho position with respect to each other.

In the general formula (I), $R^2$ represents one or two monovalent substituents present on a benzene ring, which have an anionic functional group at an end.

When a plurality of $R^2$s are present, $R^2$s are the same or different.

In particular, the "group having an anionic functional group at an end" in the general formula (I) is preferably a group consisting only of an anionic functional group because of easy synthesis.

The anionic functional group is preferably one selected from the group consisting of a carboxy group, a sulfonic acid group and a phosphoric acid group, particularly preferably a sulfonic acid group.

The number of $R^2$s is 1 or 2, preferably 1. When there are two $R^2$s, $R^2$s are the same or different from each other. In particular, when there are two $R^2$s, it is preferable that $R^2$s are the same because of easy synthesis.

In particular, since there is a significant difference between the maximum absorption wavelengths of the compound of the general formula (I) (non-dissociation type (neutral type)) and the compound after desorption of a part containing a phosphoric acid group (dissociation type (anion type)), $R^2$ is present preferably at the 3- or 5-position, more preferably at the 3-position when in the general formula (I), the xanthene backbone is at the 1-position, one $R^1$ is at the 4-position and the other $R^1$ is at the 6-position in a benzene ring having two $R^1$s and one $R^2$.

In a preferred aspect of the compound of the general formula (I), it is preferable that two methoxy groups are present as $R^1$ and one sulfonic acid group is present as $R^2$.

In addition, in a preferred aspect of the compound of the general formula (I), it is preferable that as $R^1$, two methoxy groups are present at the 4- and 6-positions, and as $R^2$, one sulfonic acid group is present at the 3-position.

In the general formula (I), $R^3$ and $R^4$ each independently represent a hydrogen atom, an alkyl group having 1 to 6 carbon atoms, or a halogen atom.

When $R^3$ or $R^4$ represents an alkyl group, the alkyl group may have one or more halogen atoms, carboxy groups, sulfonyl groups, hydroxyl groups, amino groups, alkoxy groups and the like, and for example, the alkyl group represented by $R^3$ or $R^4$ may be an alkyl halide group, a hydroxyalkyl group, a carboxyalkyl group or the like. It is preferable that $R^3$ and $R^4$ each independently represent a hydrogen atom or a halogen atom, and it is more preferable that both $R^3$ and $R^4$ are hydrogen atoms, or both $R^3$ and $R^4$ are fluorine atoms or chlorine atoms.

In the general formula (I), $R^5$ and $R^6$ each independently represent an alkyl group having 1 to 6 carbon atoms, or an aryl group.

It is preferable that $R^5$ and $R^6$ each independently represent an alkyl group having 1 to 3 carbon atoms, and it is more preferable that both $R^5$ and $R^6$ are methyl groups. The alkyl groups represented by $R^5$ and $R^6$ may have one or more halogen atoms, carboxy groups, sulfonyl groups, hydroxyl groups, amino groups, alkoxy groups and the like, and for example, the alkyl group represented by $R^5$ or $R^6$ may be an alkyl halide group, a hydroxyalkyl group, a carboxyalkyl group or the like.

When $R^5$ or $R^6$ is an aryl group, the aryl group may be either a monocyclic aromatic group or a condensed aromatic group, and the aryl ring may contain one or more ring forming hetero atoms (e.g. nitrogen atom, oxygen atom or sulfur atom). The aryl group is preferably a phenyl group. One or more substituents may be present on the aryl ring. As the substituent, for example, one or more halogen atoms, carboxy groups, sulfonyl groups, hydroxyl groups, amino groups, alkoxy groups and the like may be present.

In the general formula (I), $R^2$ and $R^8$ each independently represent a hydrogen atom, an alkyl group having 1 to 6 carbon atoms, or a halogen atom, and are the same as those described for $R^3$ and $R^4$. It is preferable that both $R^7$ and $R^8$ are hydrogen atoms, chlorine atoms or fluorine atoms.

In the general formula (I), X is a silicon atom, a phosphorus atom, a germanium atom or a tin atom, and is preferably a silicon atom.

In the general formula (I), Z is an oxygen atom or $N^+R^9R^{10}$.

When Z is $N^+R^9R^{10}$, $R^9$ and $R^{10}$ each independently represent a hydrogen atom, or an alkyl group having 1 to 10 carbon atoms.

The alkyl group having 1 to 10 carbon atoms is preferably a linear alkyl group, more preferably a methyl group or an ethyl group.

In addition, $R^9$ and $R^{10}$ are optionally linked together to form a four- to seven-membered heterocyclyl containing a nitrogen atom bonded to $R^9$ and $R^{10}$.

In addition, $R^9$ or $R^{10}$, or each of both $R^9$ and $R^{10}$ is optionally linked with $R^4$ or $R^9$ to form a five- to seven-membered heterocyclyl or heteroaryl containing a nitrogen atom bonded to $R^9$ or $R^{10}$, and optionally contains one to three additional hetero atoms selected from the group consisting of an oxygen atom, a nitrogen atom and a sulfur atom as ring forming members, and the heterocyclyl or heteroaryl is optionally substituted with an alkyl having 1 to 6 carbon atoms, an alkenyl having 2 to 6 carbon atoms, an alkynyl having 2 to 6 carbon atoms, an aralkyl group having 6 to 10 carbon atoms, or an alkyl-substituted alkenyl group having 6 to 10 carbon atoms.

Examples of the heterocyclyl or heteroaryl thus formed include, but are not limited to, pyrrolidine, piperidine, hexamethyleneimine, pyrrole, imidazole, pyrazole, oxazole and thiazole.

When Z is an oxygen atom, Y is preferably a single bond, $—O—(CH_2)_{n1}—$ or $—O—(CH_2)_{n2}—Ar_1—$, and when Z is $N^+R^9R^{10}$, Y is preferably a single bond, $—NH—(CH_2)_{n3}—$ or $—NH—(CH_2)_{n4}—Ar_2—$.

In the general formula (I), Y is a single bond, $—O—(CH_2)_{n1}—$, $—O—(CH_2)_{n2}—Ar_1—$, $—NH—(CH_2)_{n3}—$ or $—NH—(CH_2)_{n4}—Ar_2—$.

In Y, a bonding hand of —O— or —NH— on a side opposite to the alkylene group is bonded to a carbon atom forming a heterocyclic three-membered ring in the general formula (I). In addition, a bonding hand of $—(CH_2)—$, $—Ar_1—$, $—(CH_2)_{n3}—$ or $—Ar_2—$ on a side opposite to the oxygen atom (O), the amino group (NH) or the alkylene group is bonded to a phosphoric acid group in the general formula (I).

n1, n2, n3 and n4 each independently represent an integer of 1 to 10.

$Ar_1$ and $Ar_2$ each independently represent a substituted or unsubstituted arylene group.

n1, n2, n3 and n4 each represent the number of repetitions of the alkylene group in Y. n1, n2, n3 and n4 are each preferably an integer of 1 to 8, more preferably an integer of 1 to 6, still more preferably an integer of 1 to 4, particularly an integer of 1 or 2.

The unsubstituted arylene group in $Ar_1$ and $Ar_2$ is preferably one having 6 to 14 carbon atoms, and specific examples thereof include a phenylene group and a naphthylene group. In particular, the unsubstituted arylene group in $Ar_1$ and $Ar_2$ is preferably a phenylene group.

Examples of the substituent in the arylene group include halogen atoms, and alkyl groups having 1 to 10 carbon atoms.

The halogen atom is preferably a chlorine atom, a bromine atom or an iodine atom.

The alkyl group having 1 to 10 carbon atoms is preferably a linear alkyl group, more preferably a methyl group or an ethyl group.

In the general formula (I)

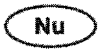

(Nu) is a partial structure of a nucleoside in which a sugar is bonded to an organic base via a glycoside bond, and is represented by R—S—.

Here, R represents an organic base, and S represents a sugar moiety of the nucleoside.

ENPP is an enzyme that hydrolyzes substrates such as nucleotide triphosphate, and unlike alkaline phosphotase which breaks the structure of phosphate itself, ENPP has an action mechanism having the characteristic of recognizing the structure a nucleic acids and breaking a phosphate bond.

In the present invention, with attention given to this point, a structure that can be a new enzyme substrate is introduced to a phosphoric acid monoester site that is an enzyme recognition site in a conventional microdevice-compatible fluorescent probe In this way, the fluorescent probe of the present invention is metabolized to ENPP having a nucleic acid as a substrate, and can cause an increase in fluorescence intensity.

In addition, in the general formula (I),

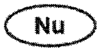

(Nu) may be an organic base which is an amine or an ammonium salt. Here, in R—S, R represents an organic base which is an amine or an ammonium salt, and S represents a single bond (i.e. R is directly bonded to the phosphoric acid ester).

Here, it is preferable that the organic base of R is selected from the group consisting of a nucleic acid base and a derivative thereof; and a partial structure of choline ($(CH_3)_3N^+$—$C_2H_4$—), a diethylamino group ($(CH_3CH_2)_2N$—), and an amino group represented by an amino group ($R_2N$—), or an ammonium group.

In $R_2N$—, R represents a hydrogen atom, or an alkyl group having 1 to 10 carbon atoms, the two Rs are the same or different, it is preferable that one R or each of both Rs represents a hydrogen atom or a methyl group, and it is more preferable that both Rs are hydrogen atoms or methyl groups.

Here, when the organic base of R is the amino group or ammonium group, S represents a single bond.

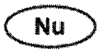

Even the fluorescent probe of the present invention which contains such an organic base can be recognized by ENPP as a structure similar to that of a nucleic acid, and the phosphate bond can be broken to cause an increase in fluorescence intensity.

It is preferable that the nucleic acid base is selected from the group consisting of adenine, thymine, cytosine, guanine and uracil.

S represents a sugar moiety of the nucleoside, which is a sugar or a partial structure of a derivative thereof.

The sugar of S or a derivative thereof is preferably ribose, deoxyribose, or a derivative thereof.

In addition, when the organic base of R is the amino group or ammonium group, S represents a single bond.

Ribose, deoxyribose or derivatives thereof are bonded to an organic base at the 1'-position and a phosphate bond at the 5'-position.

In one preferred aspect of the present invention, R—S— is selected from:

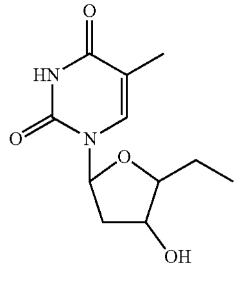

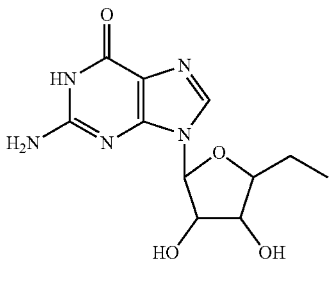

-continued

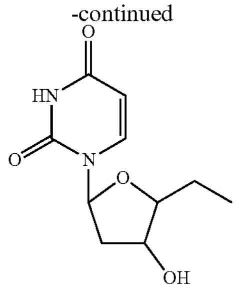

$(CH_3)_3N^+$—$C_2H_4$—;

$(CH_3CH_2)_2N$—; and $R_2N$— (R represents a hydrogen atom or an alkyl group having 1 to 10 carbon atoms, and Rs are the same or different).

2. Compound of General Formula (II) or Derivative Thereof

Another embodiment of the present invention is a compound of the following general formula (II), or a salt thereof.

(II)

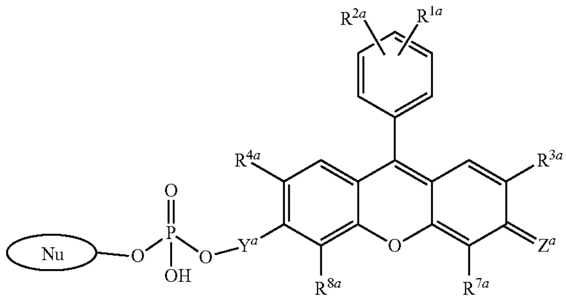

In the general formula (II), $R^{1a}$ represents one or two monovalent substituents present on a benzene ring, which are electron donating groups, and when a plurality of $R^{1a}$s are present, $R^{1a}$s are the same or different.

Details of $R^{1a}$ are the same as those of $R^1$ in the general formula (I).

In the general formula (II), $R^{2a}$ represents one or two monovalent substituents present on a benzene ring, which have an anionic functional group at an end, and when a plurality of $R^{2a}$s are present, $R^{2a}$s are the same or different.

Details of $R^{2a}$ are the same as those of $R^2$ in the general formula (I).

In the general formula (II), $R^{3a}$ and $R^{4a}$ each independently represent a hydrogen atom, an alkyl group having 1 to 6 carbon atoms, or a halogen atom.

Details of $R^{3a}$ and $R^{4a}$ are the same as those of $R^3$ and $R^4$ in the general formula (I).

In the general formula (II), $R^{7a}$ and $R^{8a}$ each independently represent a hydrogen atom, an alkyl group having 1 to 6 carbon atoms, or a halogen atom.

Details of $R^{7a}$ and $R^{8a}$ are the same as those of $R^7$ and $R^3$ in the general formula (I).

In general formula (II), $Z^a$ represents an oxygen atom or $N^+R^{9a}R^{10a}$.

Here, $R^{9a}$ and $R^{10a}$ each independently represent a hydrogen atom, or an alkyl group having 1 to 10 carbon atoms.

The alkyl group having 1 to 10 carbon atoms is preferably a linear alkyl group, more preferably a methyl group or an ethyl group.

In addition, $R^{9a}$ and $R^{10a}$ are optionally linked together to form a four- to seven-membered heterocyclyl containing a nitrogen atom bonded to $R^{9a}$ and $R^{10a}$.

In addition, $R^{9a}$ or $R^{10a}$, or each of both $R^{9a}$ and $R^{10a}$ is optionally linked with $R^{4a}$ or $R^{8a}$ to form a five- to seven-membered heterocyclyl or heteroaryl containing a nitrogen atom bonded to $R^{9a}$ or $R^{10a}$. optionally contains one to three additional hetero atoms selected from the group consisting of an oxygen atom, a nitrogen atom and a sulfur atom as ring forming members, and the heterocyclyl or heteroaryl is optionally substituted with an alkyl having 1 to 6 carbon atoms, an alkenyl having 2 to 6 carbon atoms, an alkynyl having 2 to 6 carbon atoms, an aralkyl group having 6 to 10 carbon atoms, or an alkyl-substituted alkenyl group having 6 to 10 carbon atoms.

Examples of the heterocyclyl or heteroaryl thus formed include, but are not limited to, pyrrolidine, piperidine, hexamethyleneimine, pyrrole, imidazole, pyrazole, oxazole and thiazole.

In the general formula (II), $Y^a$ is a single bond, $—O—(CH_2)_{n1}—$, $—O—(CH_2)_{n2}—Ar_1—$, $—NH—(CH_2)_{n3}—$ or $—NH—(CH_2)_{n4}—Ar_2—$, and here, n1, n2, n3 and n4 each independently represent an integer of 1 to 10.

$Ar_1$ and $Ar_2$ each independently represent a substituted or unsubstituted arylene group.

Details of n1, n2, n3, n4, $Ar_1$ and $Ar_2$ are the same as those of n1, n2, n3, n4, $Ar_1$ and $Ar_2$ in the general formula (I).

In the general formula (II)

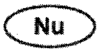

is represented by R—S— where R represents an organic base,

S represents a sugar, or a partial structure of a derivative thereof, or a single bond. Details of R and S are the same as those described in the general formula (I).

The compound of the general formula (I) or (II) may have one or more asymmetric carbons depending on the type of substituent, and a stereoisomer such as an optical isomer or a diastereoisomer may be present. Stereoisomers in pure form, any mixture of stereoisomers, racemates and the like are all within the scope of the present invention. The compound of the general formula (I) or (II) or a salt thereof may be present as a hydrate or a solvate, and any of these substances is within the scope of the present invention. The type of solvent forming the solvate is not particularly limited, and examples thereof include solvents such as ethanol, acetone and isopropanol.

A method for producing a typical compound among the compounds of the present invention is shown in detail in examples herein. Therefore, those skilled in the art can produce a compound of the present invention by appropriately selecting reaction materials, reaction conditions, reaction reagents and the like in accordance with the descriptions given herein, and making a modification and a change to the methods if necessary.

3. Fluorescent Probe for Detecting ENPP

One embodiment of the present invention is a fluorescent probe for detecting ENPP, which comprises a compound of the general formula (I) or a salt thereof.

Another embodiment of the present invention is a fluorescent probe for detecting ENPP, which comprises a compound of the general formula (II) or a salt thereof.

Hereinafter, the compound of the general formula (I) or a salt thereof and the compound of the general formula (II) or a salt thereof are also referred to collectively as a compound of the present invention or a salt thereof.

Another aspect of the present invention is a method for detecting the intracellular activity of ENPP, comprising the steps of (a) introducing a compound of the present invention or a salt thereof into a cell, and (b) measuring fluorescence emitted by reaction of the compound or a salt thereof with ENPP in the cell.

The compound of the present invention or a salt thereof has a characteristic of having substantially no fluorescence or only weak fluorescence in an environment free of aldehyde dehydrogenase 1A1, and emitting intense fluorescence in an environment where ENPP is present.

The method of the present invention may further comprise observing a fluorescent response using fluorescence imaging means. As the means for observing the fluorescent response, a fluorometer with a wide range of measurement wavelengths can be used, and the fluorescent response can also be visualized by using fluorescence imaging means capable of displaying the fluorescent response as a two-dimensional image. Since the fluorescent response can be two-dimensionally visualized by using fluorescence imaging means, ENPP can be visually recognized instantly. As a fluorescence imaging apparatus, an apparatus known in the art can be used. In some cases, it is also possible to detect a reaction between the sample to be measured and the fluorescent probe by a change in ultraviolet visible light absorption spectrum (e.g. a change in absorbance at a specific absorption wavelength).

The method for using the fluorescent probe of the present invention is not particularly limited, and the fluorescent probe can be used as in the case of a heretofore known fluorescent probe. Typically, the compound of the present invention or a salt thereof is dissolved in an aqueous medium such as physiological saline or a buffer solution, a mixture of an aqueous medium with a water-miscible organic solvent such as ethanol, acetone, ethylene glycol, dimethylsulfoxide or dimethylformamide, or the like, the resulting solution is added to a suitable buffer solution containing cells and tissues, and a fluorescence spectrum is measured. The fluorescent probe of the present invention may be combined with suitable additives and used in the form of a composition. For example, the fluorescent probe can be combined with additives such as a buffer, a solubilizer and a pH adjuster.

The cell sample to be measured in the step (a) can be a cell expressing ENPP, and when the cell is a cancer cell or a cancer tissue expressing ENPP, the cancer cell or cancer tissue can be detected or visualized by the detection method of the present invention. That is, the fluorescent probe of the present invention, a composition containing the fluorescent probe, and the detection method of the present invention can also be used for prediction or diagnosis of cancer.

As used herein, the term “cancer tissue” means any tissue that contains cancer cells. The term “tissue” should be interpreted in the broadest sense, including part or all of the organ, and should not be interpreted in a limited way in any sense. The cancer tissue is preferably a tissue expressing ENPP at a high level. In addition, the term “diagnosis” herein needs to be interpreted in the broadest sense including visual or microscopic confirmation of the presence of a cancer tissue at any biological site.

In the detection method of the present invention, it is preferable to use an ENPP detection kit comprising the fluorescent probe. In the kit, the fluorescent probe of the present invention is typically prepared as a solution, and can be provided as a composition in an appropriate form such as, for example, a powdered mixture, a freeze-dried product, a granule, a tablet or a solution, and dissolved in distilled water for injection or an appropriate buffer solution at the time of use.

In addition, the kit may appropriately contain other reagents and the like if necessary. For example, as additives, additives such as a solubilizing agent, a pH adjusting agent, a buffering agent and an isotonizing agent can be used, and the blended amounts thereof can be appropriately selected by a person skilled in the art.

The fluorescent probe for detecting ENPP according to the present invention can be used in a method for detecting the enzyme activity of ENPP in a biological sample when provided in wells of a microdevice described later.

That is, one preferred embodiment of the present invention is a fluorescent probe for detecting ENPP, which contains the compound of the present invention and is used for microdevices.

Another preferred embodiment of the present invention is a fluorescent probe for detecting ENPP, which comprises the compound of the present invention and is used in a method for detecting enzyme activity using a microdevice.

4. Microdevice

A microdevice according to an embodiment of the present invention comprises the fluorescent probe for detecting ENPP.

The microdevice of the present embodiment enables detection of the enzyme activity of ENPP in a biological sample with high quantitativeness and sensitivity.

The material of the microdevice is not particularly limited, and examples thereof include glass materials, silicon, and plastics including dendritic polymers or copolymers. Examples of the glass material include soda-lime glass, Pyrex (registered trademark) glass, Vycor (registered trademark) glass and quartz glass. Examples of the resin polymer include poly(vinyl chloride), poly(vinyl alcohol), poly(methyl methacrylate), poly(vinyl acetate-co-maleic anhydride), poly(dimethylsiloxane)monomethacrylate, cyclic olefin polymers, fluorocarbon polymers, polystyrene, polypropylene and polyethyleneimine. Examples of the copolymer include poly(vinyl acetate-co-maleic anhydride), poly (styrene-co-maleic anhydride), poly(ethylene-co-acrylic acid) and derivatives thereof.

Examples of the shape of the microdevice include multiwell plates in which a certain number of wells (e.g. microwells) are arranged as shown in FIG. 1. The number of wells per plate is, for example, 1 or more and 10,000,000 or less, 10 or more and 500,000 or less, or about 100,000 per plate.

The pore diameter of the well of the microdevice according to the present embodiment may be, for example, 10 nm or more and 10 μm or less, 100 nm or more and 10 μm or less, or 1 μm or more and 10 μm or less.

The depth of the well of the microdevice according to the present embodiment may be, for example, 10 nm or more and 1 μm or less, 100 nm or more and 800 μm or less, or 200 nm or more and 700 nm or less.

When the pore diameter and depth are within the above-described ranges, one molecule of ENPP can be held in the well, and the enzyme activity of each molecule of ENPP in the biological sample can be detected.

In the microdevice according to the present embodiment, one type of the fluorescent probe for detecting ENPP may be provided in one well.

Accordingly, for one molecule of ENPP in a biological sample, the fluorescence intensity of one type of fluorescent probe for detecting ENPP can be detected to compare the enzyme activities of ENPP molecules.

In addition, the microdevice according to the present embodiment may include two or more types of the fluorescent probes for detecting ENPP, which have different reaction points in one well and different fluorescence wavelengths.

As used herein, the phrase "having different reaction points" means that positions of breakage by ENPP are different, i.e. lengths between the mother nucleus of a compound which emits fluorescence (e.g. rhodamine backbone) and a phosphoric acid group hydrolyzed by ENPP are different, or organic bases and derivatives thereof, or sugars and derivatives thereof are different. Specifically, examples of the two types of fluorescent probes for detecting ENPP which have different reaction points and different fluorescence wavelengths include the compounds shown below.

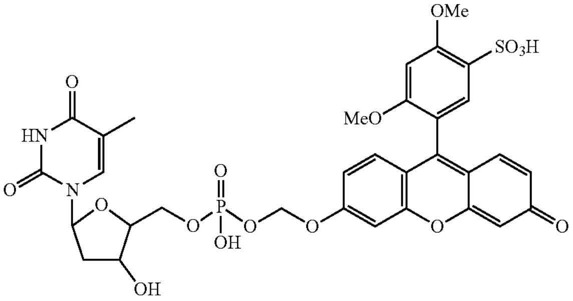

sTG-mdTMP

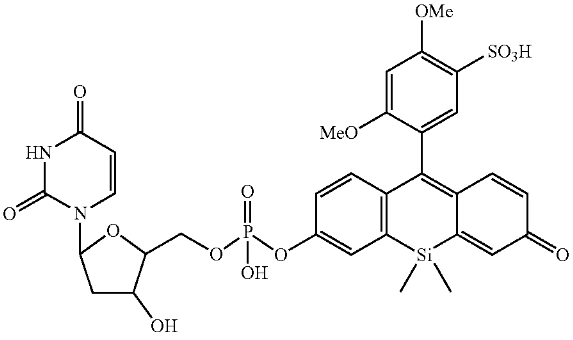

sTM-dCMP

ENPP is known to have subtypes such as ENPP1, ENPP2, ENPP3, ENPP4, ENPP5, ENPP6 and ENPP7. The characteristics of the subtype are as shown below.

| molecules | substrates | expression sites | functions |
|---|---|---|---|
| NPP6 | lysophopholipids | brain<br>kidney | unknown |
| NPP4 | unknown | ubiquitous | unknown |
| NPP5 | unknown | brain | unknown |
| NPP7 | lysophopholipids | small intestine | unknown |
| NPP1 | nucleotides | ubiquitous | multifunction[1] |
| NPP2/ATX | lysophopholipids | ubiquitous | multifunction[2] |
| NPP3 | unknown | ubiquitous | basophil marker |

*J. Am. Chem. Soc*, 2011, 133, 12021-12030.

By providing two or more types of the fluorescent probes for detecting ENPP which have different reaction points in one well and different fluorescence wavelengths, the subtype of ENPP can be classified from patterns of fluorescence intensity.

Further, a microdevice comprising two or more types of fluorescent probes for detecting ENPP which have different reaction points in one well and different fluorescence wavelengths can be applied for discovery of a disease-specifically found ENPP subtype and diagnosis of disease by performing an ENPP fluorescence assay on biological samples derived from a healthy person and a subject with a disease.

The amount of fluorescent probes for detecting ENPP which are contained in one well of the microdevice according to the present embodiment may be, for example, 100 nM or more and 100 μM or less, 1 μM or more and 100 μM or less, or 10 μM or more and 100 μM or less.

As a method for using the microdevice according to the present embodiment, first, a solution containing a biological sample is added to the microdevice. Sealing oil is then added dropwise for encapsulating the ENPP in the biological sample in the wells of the microdevice.

5. Test Kit for Enzyme Activity of ENPP

Another embodiment of the present invention is a test kit for enzyme activity of ENPP, which comprises the compound of the present invention.

Another embodiment of the present invention is a kit comprising the compound of the invention and a plate provided with microwells containing the compound.

One preferred aspect of the kit of the present invention includes two or more types of the fluorescent probes for detecting ENPP which have different reaction points in one well and different fluorescence wavelengths.

The plate used in the kit of the present invention has a certain number of microwells (e.g. 1 or more and 10,000,000 or less, 10 or more and 500,000 or less, or about 1,000,000).

In the kit of the present invention, it is preferable that the microwell can hold one molecule of ENPP.

Figure 2:
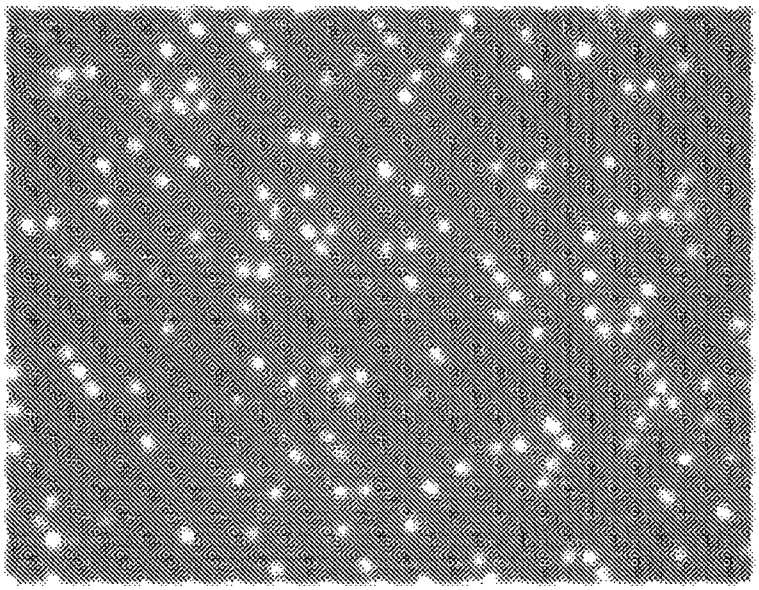
FIG. 2 shows an example of a microscopic image of a microdevice containing an enzyme and a fluorescent probe.

Specifically, the plate used in the kit of the present invention has a structure in which millions of minute wells are arranged. A sufficiently diluted enzyme solution is added to the wells to create conditions which ensure that only one molecule or less of an enzyme is present in each well, and the activity of the enzyme can be detected as a signal. FIG. 2 shows an example of an image in which the enzyme is detected in the manner described above. This image is a microscopic image of a microdevice to which an enzyme and a fluorescent probe have been added. The bright spots correspond to wells containing the enzyme, and the other spots correspond to wells which do not contain the enzyme.

By using the kit of the present invention, ENPP in a biological sample can be isolated and detected by one molecule. The specific method thereof will be described below.

Figure 3A:
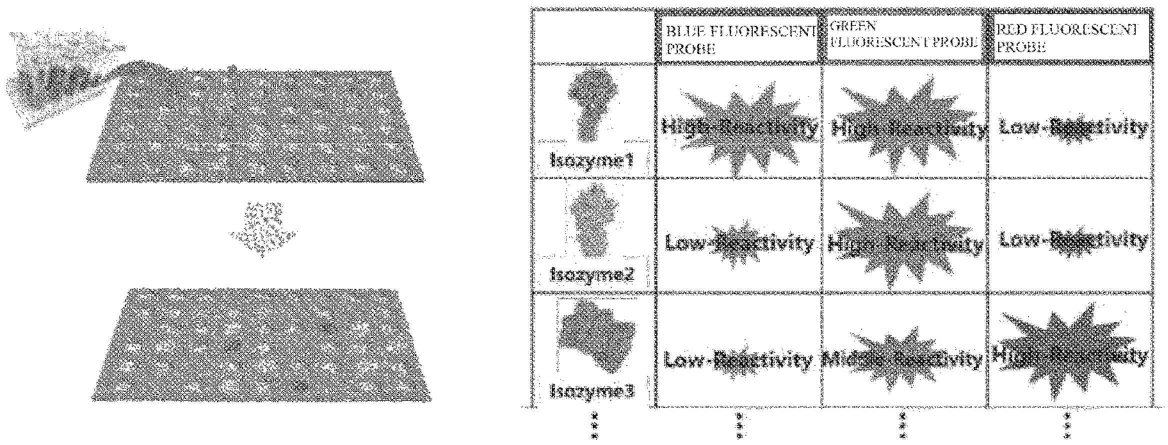
FIG. 3A is a schematic diagram of a method for isolating and detecting ENPP in a biological sample by one molecule by using the kit of the present invention.

First, a biological sample is sufficiently diluted and added to the microdevice to create a state in which one molecule or less of the enzyme is present in one well. Fluorescent probes of a plurality of colors whose reactivity varies depending on enzymes are reacted in parallel, an increase in fluorescence at a plurality of wavelengths in each well is then measured, and the enzyme contained in the well is specified from a combination of the measured values. For example, a well with a marked increase in red fluorescence may contain Isozyme3 which is highly reactive with the red probe (see FIG. 3A).

Figure 3B:
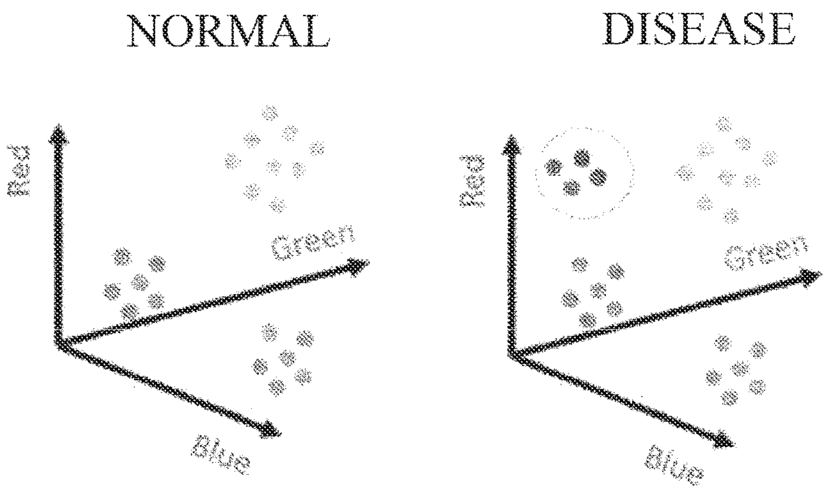
FIG. 3B is a schematic diagram of a method for isolating and detecting ENPP in a biological sample by one molecule by using the kit of the present invention.

Next, fluorescence intensity at each wavelength is measured for each of more than 100,000 wells present in the microdevice, and plotted on a point diagram to visualize the activity pattern of an enzyme in the biological sample. Since one well contains one molecule of an enzyme, it is possible to determine the number of molecules of the enzyme in the biological sample by counting the number of plots forming the cluster (see FIG. 3B).

By using such an analysis method, ENPP in the biological sample is isolated and detected by one molecule, and a cluster specific to a patient with a disease and an overall pattern are found to contribute to diagnosis.

6. Method for Detecting Enzyme Activity of ENPP in Biological Sample

The method for detecting the enzyme activity of ENPP according to an embodiment of the present invention is a method using the above-described compound. The method for detecting the enzyme activity of ENPP according to an embodiment of the present invention enables detection of the enzyme activity of ENPP in a biological sample. According to the present invention, the method for detecting the enzyme activity of ENPP in a biological sample according to an embodiment of the present invention can be a method using the above-described microdevice.

The present invention provides a method for detecting the enzyme activity of ENPP, comprising bringing a sample containing ENPP or possibly containing ENPP (e.g. a biological sample, a biopsy sample, a body fluid sample or an aqueous solution isolated from a subject) into contact with the above-described compound. In a certain aspect, the biological sample can be a blood sample (e.g. a serum sample, or a plasma sample). This method can further include measuring the fluorescence of the compound after the contact of the compound with the aqueous solution. When the compound emits fluoresces, the presence or absence of the fluorescence indicates whether the activity of ENPP is present in the aqueous solution, and the intensity of the fluorescence indicates the intensity of the activity of ENPP in the aqueous solution.

One aspect of the present invention is a method for measuring the enzyme activity of ENPP, comprising bringing the compound of the present invention into contact with ENPP.

In one preferred aspect of the method for measuring the enzyme activity of ENPP according to the present invention, the contact is performed in the presence of serum.

The present invention also provides a method for predicting the possibility that a subject has cancer, the method comprising bringing a biological sample obtained from the subject into contact with the compound, and detecting the fluorescence of the compound after the contact, in which when fluorescence is detected, the subject from which the biological sample is derived may have cancer expressing ENPP. In a certain embodiment, the prediction method of the present invention is an in vitro method. In some embodiments, the prediction method of the present invention is an industrially available method (or non-medical practice). In a certain embodiment, the cancer can be pancreas cancer.

An aspect of the present invention is a method for detecting the enzyme activity of ENPP3, comprising bringing ENPP3 into contact with the following compound (A) and/or the following compound (B).

(A)

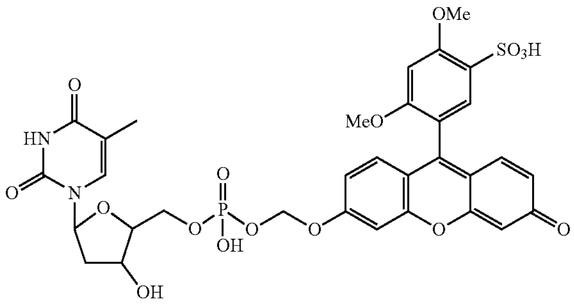

(B)

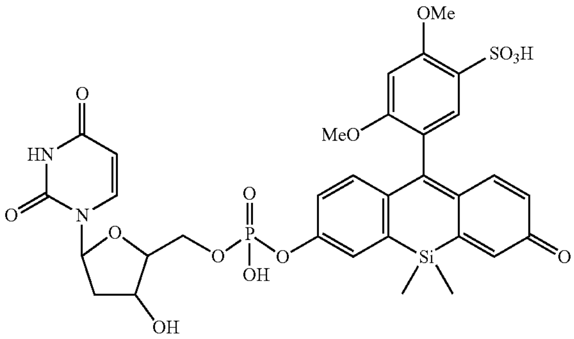

In one aspect of the method for detecting the enzyme activity of ENPP3 according to the present invention, the contact is a contact of ENPP3 with both the compound (A) and the compound (B).

The detection method of the present embodiment enables detection of the enzyme activity of ENPP in a biological sample.

The detection method of the present embodiment will be described in detail below.

[Step 1]

First, a solution containing a biological sample is added to the microdevice including the fluorescent probe for detecting ENPP. Examples of the biological sample include biological samples similar to those exemplified in "Fluorescent probe for detecting ENPP" above.

The pH of the solution containing the biological sample may be a value close to that in the living body, and specifically, the pH may be, for example, 6.0 or more and 8.0 or less.

The protein concentration of the biological sample may be, for example, 1 μM or more and 100 μM or less, for example 10 μM or more and 100 μM or less.

Examples of the method for measuring the protein concentration of a biological sample include methods using an antibody-antigen reaction (e.g. ELISA method), and colorimetric methods using a reaction of a protein with a reagent (e.g. biuretoninic acid (BCA) method, Bradford method, Lowry method and Biuret method).

The biological sample may be diluted to the above-described concentration with any of various aqueous solvents or the like. Examples of the aqueous solvent include, but are not limited to, water, physiological saline, phosphate buffered saline (PBS), tris buffered saline (TBS), and HEPES buffered saline.

[Step 2]

Subsequently, sealing oil is added dropwise for encapsulating the ENPP in the biological sample in the wells of the microdevice including the fluorescent probe for detecting ENPP. The sealing oil may be known sealing oil which is typically used for encapsulating a sample in a microdevice, and examples thereof include fluorine-based oils (FC-40 etc.).

[Step 3]

Subsequently, fluorescence in the wells of the microdevice is detected using a fluorescence scanner. The enzyme activity can be evaluated from the intensity of the detected fluorescence.

In addition, use of a microdevice including two or more types of fluorescent probes for detecting ENPP which have different reaction points in one well and different fluorescence wavelengths is advantageous for application for discovery of a disease-specifically found ENPP subtype and diagnosis of disease by comparing the enzyme activities of ENPP in biological samples derived from a healthy person and a subject with a disease.

In particular, when a microdevice including a red fluorescent probe containing the following compound (sTM-dCMP) among the compounds of the general formula (I) and a green fluorescent probe containing the following compound (sTG-mdTMP) among the compounds of the general formula (II) is used, the enzyme activities of ENPP in biological samples derived from a healthy person and a subject with a disease are compared to discover ENPP3 found specifically in pancreas cancer, so that it is possible to provide a method for diagnosing pancreas cancer (or a method for predicting the possibility that a subject from which the biological sample is derived has pancreas cancer).

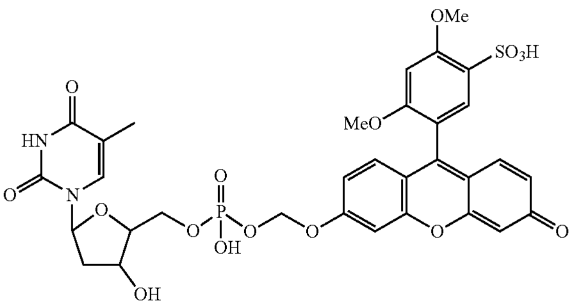

sTG-mdTMP

-continued

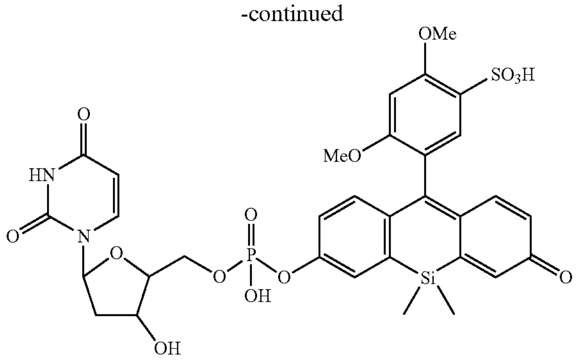

sTM-dCMP

EXAMPLES

Hereinafter, the present invention will be described by way of examples, which should not be construed as limiting the present invention.

[Sample and Measurement Method]

Reagents and solvents for organic synthesis were supplied by Tokyo Chemical Industry (TCI), Wako Purification Industry or Aldrich Chemical Co., and used without further purification.

Proton nuclear magnetic resonance (1H NMR) spectra were recorded with JEOL JMN-LA400 Instrument.

The mass spectrum was measured by JEOL JMS-T100LP AccuTOF™ LC-plus 4G.

Synthesis Example 1

Synthesis of Compound (4)

Compound (4) was synthesized in accordance with the following scheme.

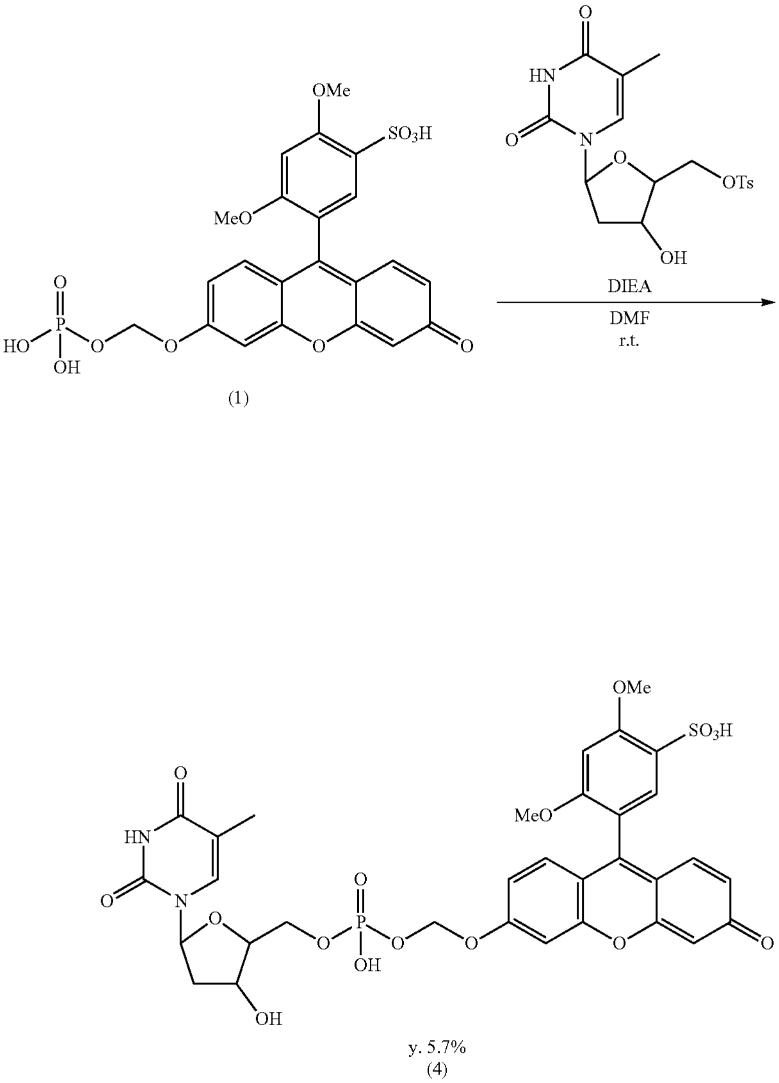

(1)

y. 5.7%

(4)

5-O-tosylthymidine (5'-O-tosylthymidine) was synthesized as described in referential literature (1). In a dry flask, 31 mg (0.078 mmol) of 5-O-tosylthymidine (5'-0-tosylthymidine) dissolved in 0.5 mL of N,N-dimethylformamide, 8.4 mg (0.016 mmol) of compound (1) and 27 μL (0.16 mmol) of N,N-diisopropylethylamine (DIEA) were added in a dry flask, and the mixture was stirred at 50° C. for 48 hours while being washed with nitrogen.

Subsequently, the solvent was distilled away by reducing pressure. Subsequently, the obtained solid was purified by HPLC (A/B=99/1→0/100 in 30 minutes, A: 0.1 M triethylamine acetate (TEAA), B: 0.1 M TEAA/80% acetonitrile/20% water, followed by A/B=90/10→0/100 in 30 minutes, A: 0.1% trifluoroacetic acid (TFA)/water, B: 0.1% TFA/acetonitrile) to obtain 0.8 mg of orange solid compound (4) (0.0011 mmol, yield 6.7).

Compound (1) was synthesized as described in Patent Literature 1 (WO 2018/159810 A1).

The results of analysis of the obtained compound by $^1$H-NMR and a high-resolution mass spectrometer (HR-MS) are shown below.

$^1$H-NMR (500 MHz, $CD_3OD$): δ 1.87 (s, 3H), 2.01-2.18 (m, 2H), 3.83 (d, 3H, J=2.3 Hz), 3.93 (d, 1H, J=10.5 Hz), 4.08-4.20 (m, 5H), 4.33-4.39 (m, 1H), 5.95 (d, 2H, J=13.8 Hz), 6.16-6.22 (m, 1H), 7.00 (s, 1H), 7.32 (dd, 1H, J=2.3, 9.2 Hz), 7.37 (d, 1H, J=2.1 Hz), 7.41-7.46 (m, 1H), 7.63 (s, 1H), 7.76 (d, 1H, J=2.2 Hz), 7.85 (d, 1H, J=5.6 Hz), 7.87-7.93 (m, 2H).

HRMS (ESI$^-$): Calcd. for $[M-H]^-$, 761.1054, Found, 761.1037 (−1.7 mmu).

Referential Literature (1)

M. Kawaguchi, T. Okabe, S. Okudaira, H. Nishimasu, R. Ishitani, H. Kojima, O. Nureki, J. Aoki, T. Nagano, Screening and X-ray crystal structure-based optimization of autotaxin (ENPP2) inhibitors, using a newly developed fluorescence probe. ACS Chem. Biol. 8, 1713-1721 (2013).

Synthesis Example 2

Synthesis of Compound (5)

Compound (5) was synthesized in accordance with the following scheme.

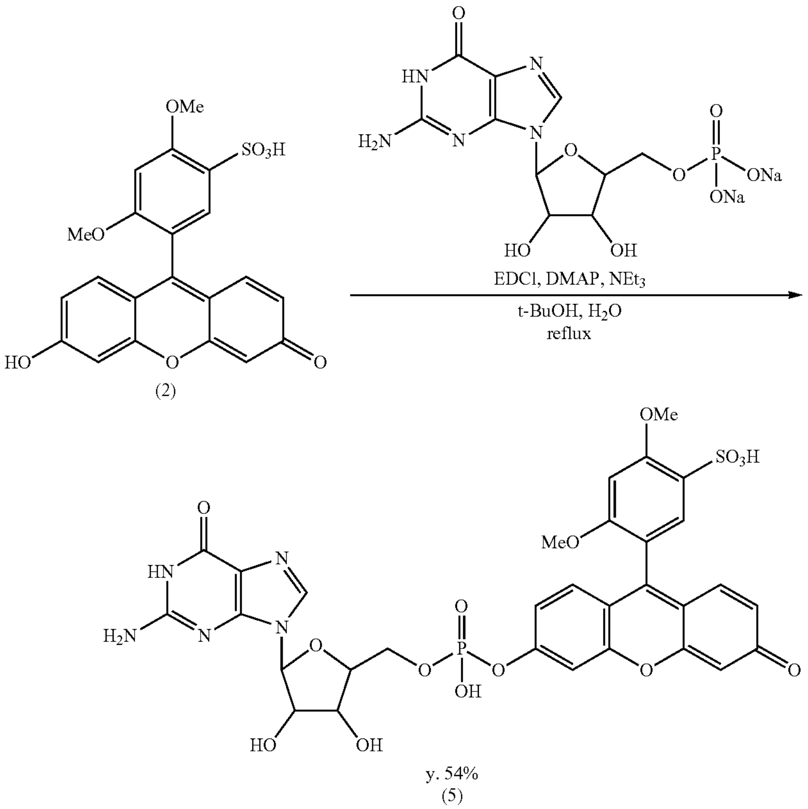

(2)

y. 54%
(5)

30 mg (0.067 mmol) of compound (2), 1 mg (0.0082 mmol) of N,N-dimethylaminopyridine (DMAP) and 2 drops of triethylamine were put in a dry flask, and the mixture was dissolved in tertiary butyl alcohol and water.

Subsequently, 28 mg (0.067 mmol) of guanosine 5'-monophosphate disodium salt) and 25 mg (0.13 mmol) of EDCI were added, and the mixture was heated under reflux for 20 minutes. Subsequently, 28 mg (0.067 mmol) of guanosine 5'-monophosphate disodium salt) and 25 mg (0.13 mmol) of EDCI were added three times at intervals of 20 minutes, and the reaction liquid was heated under reflux for 4 hours. Subsequently, the solvent was distilled away by reducing pressure. Subsequently, the obtained solid was purified by HPLC (A/B=90/10→0/100 in 30 minutes, A: 0.1% trifluoroacetic acid (TFA)/water, B: 0.1% TFA/acetonitrile) to obtain 28 mg of an orange solid compound (5) (0.036 mmol, yield 54%).

Compound (2) was synthesized as described in Patent Literature 1 (WO 2018/159810 A1).

The results of analysis of the obtained compound by $^1$H-NMR and a high-resolution mass spectrometer (HR-MS) are shown below.

$^1$H-NMR (500 MHz, DMSO-$d_6$): δ 3.76 & 3.77 (s, 3H), 3.97 (s, 3H), 4.03-4.22 (m, 5H), 4.52-4.56 (m, 1H), 5.74-5.77 (m, 1H), 6.77 (s, 1H), 6.80-6.98 (m, 3H), 7.14-7.26 (m, 2H), 7.33-7.42 (m, 2H), 7.57-7.68 (m, 2H), 8.62 & 8.65 (s, 1H), 11.04 (brs, 1H), 11.13 (brs, 1H).

HRMS (ESI$^+$): Calcd. for $[M+H]^+$, 774.1119, Found, 774.1119 (+0.0 mmu).

Synthesis Example 3

Synthesis of Compound (6)

Compound (6) was synthesized in accordance with the following scheme.

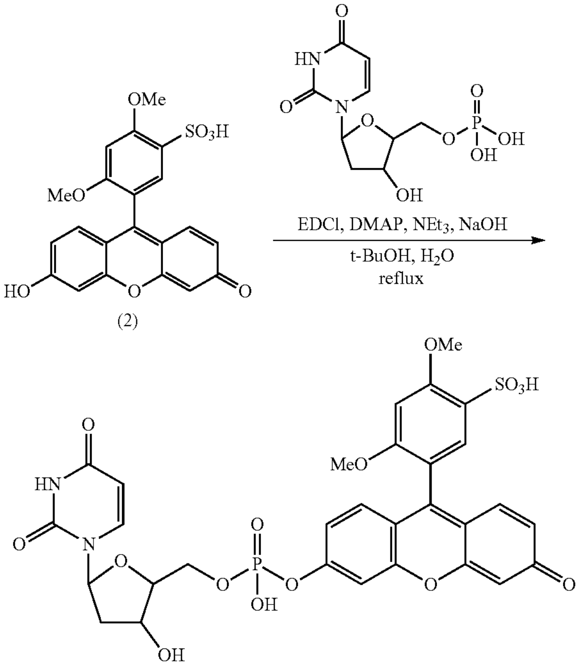

(2)

y. 47%
(6)

20 mg (0.044 mmol) of compound (2), 1 mg (0.0082 mmol) of N,N-dimethylaminopyridine (DMAP) and 2 drops of triethylamine were put in a dry flask, and the mixture was dissolved in tertiary butyl alcohol, water and a 2 N aqueous sodium hydroxide solution. Subsequently, 7.2 mg (0.022 mmol) of 2'-deoxycytidine 5'-monophosphate) and 8.4 mg (0.044 mmol) of EDCI were added, and the mixture was heated under reflux for 20 minutes. Subsequently, 7.2 mg (0.022 mmol) of 2'-deoxycytidine 5'-monophosphate) and 8.4 mg (0.044 mmol) of EDCI were added three times at intervals of 20 minutes, and the reaction liquid was heated under reflux for 4 hours. Subsequently, the solvent was distilled away by reducing pressure. Subsequently, the obtained solid was purified by HPLC (A/B=90/10→0/100 in 30 minutes, A: 0.1% trifluoroacetic acid (TFA)/water, B: 0.1% TFA/acetonitrile) to obtain 15 mg of an orange solid compound (6) (0.021 mmol, yield 47%).

The results of analysis of the obtained compound by $^1$H-NMR and a high-resolution mass spectrometer (HR-MS) are shown below.

$^1$H-NMR (500 MHz, DMSO-$d_6$): δ 2.08-2.25 (m, 2H), 3.78 (s, 3H), 3.92-4.02 (m, 1H), 3.97 (s, 3H), 4.04-4.10 (m, 1H), 4.10-4.17 (m, 1H), 4.18-4.25 (m, 1H), 5.96-6.10 (m, 2H), 6.85 (dd, 1H, J=1.7, 9.6 Hz), 6.86-6.94 (m, 2H), 7.27-7.44 (m, 3H), 7.60 (d, 1H, J=9.1 Hz), 7.68 (dd, 1H, J=2.1, 8.5 Hz), 8.01-8.12 (m, 1H), 8.53-8.65 (m, 1H), 9.56 (d, 1H, J=3.3 Hz).

HRMS (ESI$^-$): Calcd. for $[M-2H]^{2-}$, 716.0713, Found, 716.0719 (+0.6 mmu).

Synthesis Example 4

Synthesis of Compound (7)

Compound (7) was synthesized in accordance with the following scheme.

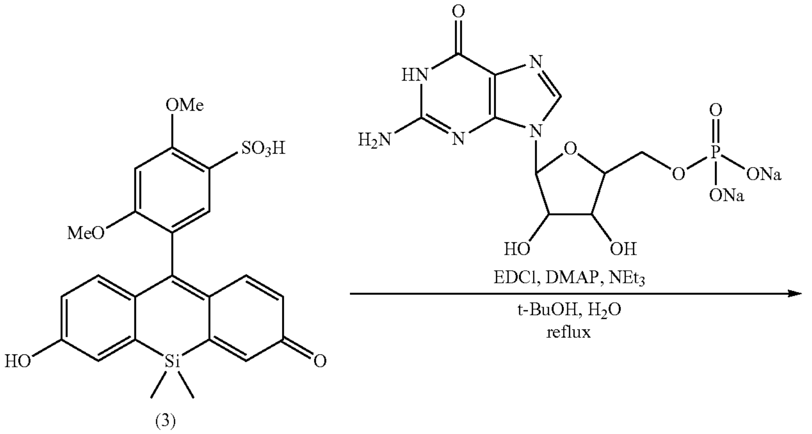

(3)

-continued

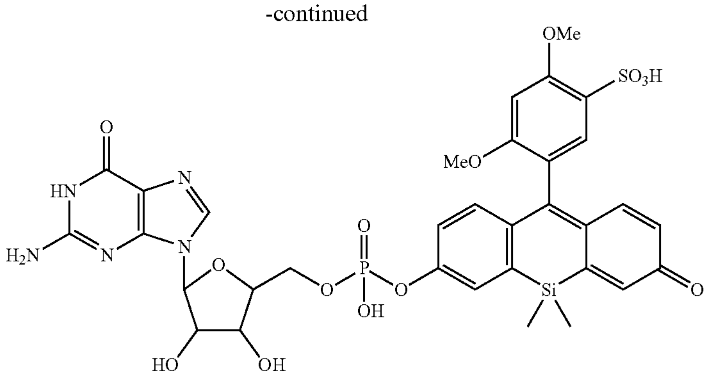

y. 9.6%
(7)

18 mg (0.038 mmol) of compound (3), 1 mg (0.0082 mmol) of N,N-dimethylaminopyridine (DMAP) and 2 drops of triethylamine were put in a dry flask, and the mixture was dissolved in tertiary butyl alcohol and water. Subsequently, 16 mg (0.038 mmol) of guanosine 5'-monophosphate disodium salt) and 14 mg (0.076 mmol) of EDCI were added, and the mixture was heated under reflux for 20 minutes. Subsequently, 16 mg (0.038 mmol) of guanosine 5'-monophosphate disodium salt) and 14 mg (0.076 mmol) of EDCI were added three times at intervals of 20 minutes, and the reaction liquid was heated under reflux for 4 hours. Subsequently, the solvent was distilled away by reducing pressure. Subsequently, the obtained solid was purified by HPLC (A/B=90/10→0/100 in 30 minutes, A: 0.1, trifluoroacetic acid (TFA)/water, B: 0.1% TFA/acetonitrile) to obtain 3 mg of an orange solid compound (7) (0.0037 mmol, yield 9.6%).

The results of analysis of the obtained compound by $^{1}$H-NMR and a high-resolution mass spectrometer (HR-MS) are shown below.

$^{1}$H-NMR (500 MHz, DMSO-$d_6$): δ 0.48 (s, 3H), 0.59 (s, 3H), 3.73 (s, 3H), 4.02 (s, 3H), 4.18-4.39 (m, 4H), 4.48-4.54 (m, 1H), 5.97 (brs, 1H), 6.04 (d, 1H, J=1.8 Hz), 6.69 (d, 1H, J=1.8 Hz), 6.74 (dd, 1H, J=2.3, 9.0 Hz), 7.08 (d, 1H, J=2.6 Hz), 7.23 (dd, 1H, J=1.8, 8.8 Hz), 7.28 (d, 1H, J=9.0 Hz), 7.35 (d, 1H, J=8.9 Hz), 7.56 (s, 1H), 9.04 (brs, 1H).

HRMS (ESI$^+$): Calcd. for $[M+H]^+$, 816.1408, Found, 816.1406 (−0.2 mmu).

Synthesis Example 5

Synthesis of Compound (8)

Compound (8) was synthesized in accordance with the following scheme.

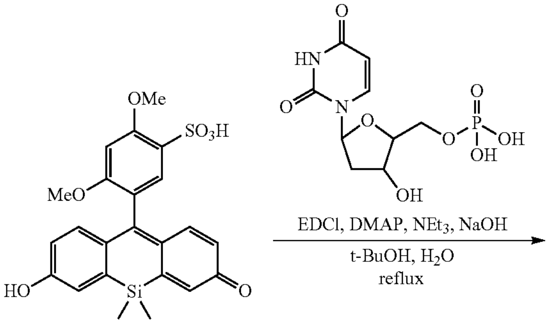

(3)

-continued

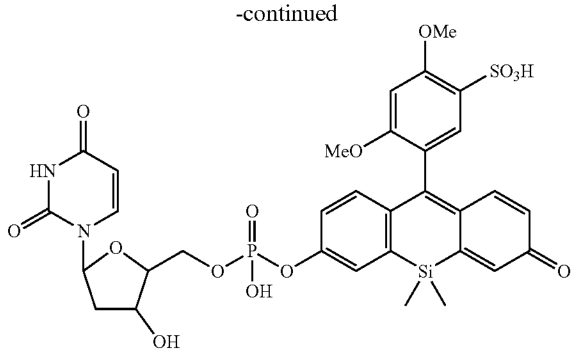

y. 71%
(8)

11 mg (0.022 mmol) of compound (3), 1 mg (0.0082 mmol) of N,N-dimethylaminopyridine (DMAP) and 2 drops of triethylamine were put in a dry flask, and the mixture was dissolved in tertiary butyl alcohol, water and a 2 N aqueous sodium hydroxide solution. Subsequently, 3.6 mg (0.011 mmol) of 2'-deoxycytidine 5'-monophosphate) and 4.2 mg (0.022 mmol) of EDCI were added, and the mixture was heated under reflux for 20 minutes. Subsequently, 3.6 mg (0.011 mmol) of 2'-deoxycytidine 5'-monophosphate) and 4.2 mg (0.022 mmol) of EDCI were added three times at intervals of 20 minutes, and the reaction liquid was heated under reflux for 4 hours. Subsequently, the solvent was distilled away by reducing pressure. Subsequently, the obtained solid was purified by HPLC (A/B=90/10-0/100 in 30 minutes, A: 0.1% trifluoroacetic acid (TFA)/water, B: 0.1% TFA/acetonitrile) to obtain 12 mg of an orange solid compound (8) (0.016 mmol, yield 71%).

The results of analysis of the obtained compound by $^{1}$H-NMR and a high-resolution mass spectrometer (HR-MS) are shown below.

$^{1}$H-NMR (500 MHz, DMSO-$d_6$): δ 0.49 & 0.51 (s, 3H), 0.60 & 0.60 (s, 3H), 2.13-2.20 (m, 1H), 2.30-2.38 (m, 1H), 3.73 & 3.74 (s, 3H), 4.02 & 4.02 (s, 3H), 4.07-4.12 (m, 1H), 4.13-4.19 (m, 1H), 4.22-4.30 (m, 1H), 4.34-4.40 (m, 1H), 5.90-5.96 (m, 1H), 6.03-6.07 (m, 1H), 6.13-6.18 (m, 1H), 6.68-6.75 (m, 2H), 7.07-7.10 (m, 1H), 7.20-7.24 (m, 1H), 7.28-7.32 (m, 1H), 7.34-7.39 (m, 1H), 7.58-7.62 (m, 1H), 8.13 (d, 1H, J=8.1 Hz).

HRMS (ESI$^-$): Calcd. for $[M-2H]^{2-}$, 758.1003, Found, 758.1019 (+1.6 mmu).

Example 1

In Vitro ENPP Fluorescence Assay

Figure 4:
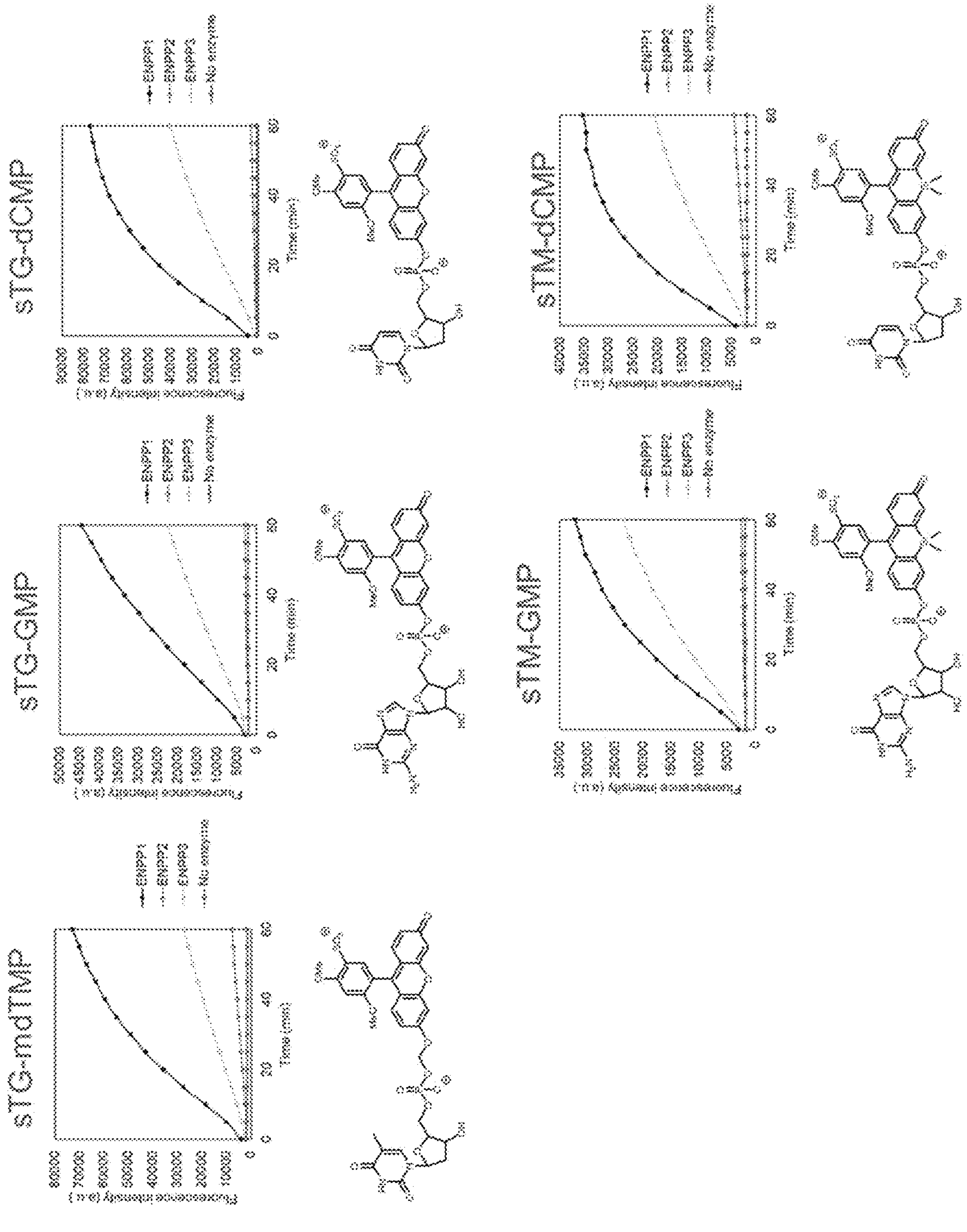
FIG. 4 shows the results of measurement in vitro fluorescence assays of compounds (4) to (8).

First, compounds (4) to (8) were each diluted to 10 μmol/L with an assay buffer. The assay buffer has the composition of Tris-HCl buffer (pH 9.0), magnesium chloride at 5.0 mmol/L and sodium chloride at 100 mmol/L. Subsequently, ENPP1, ENPP2 and ENPP3 were each added at 1 μmol/L, and the mixture was dispensed into a multi-well plate. Subsequently, the fluorescence intensity was measured with a plate reader. The results are shown in FIG. 4.

Example 2

Measurement of Human Plasma Sample Using ENPP Probe in Microdevice

Figure 5A:
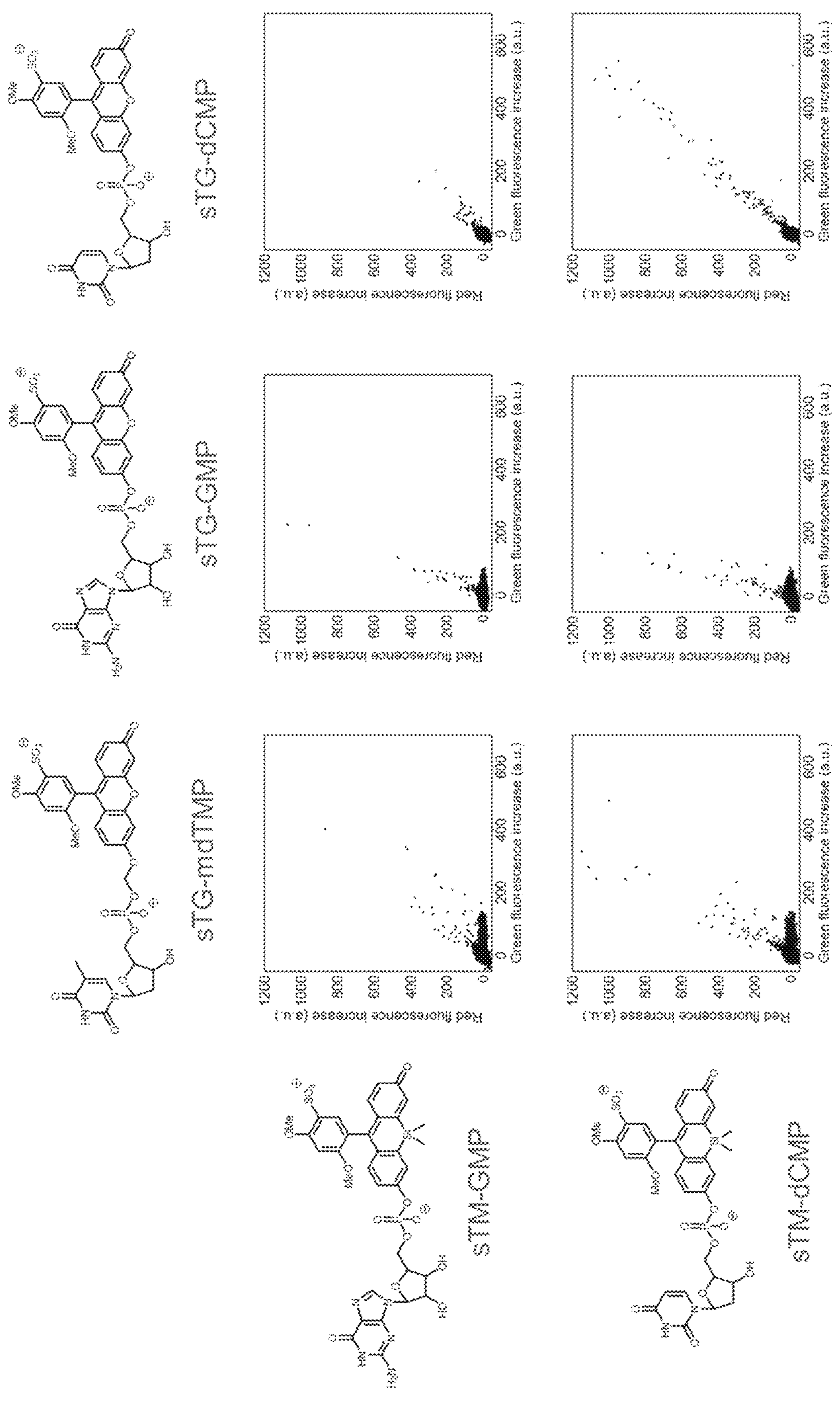
FIG. 5A shows the results of measurement of a human plasma sample using an ENPP probe in a microdevice.
Figure 5B:
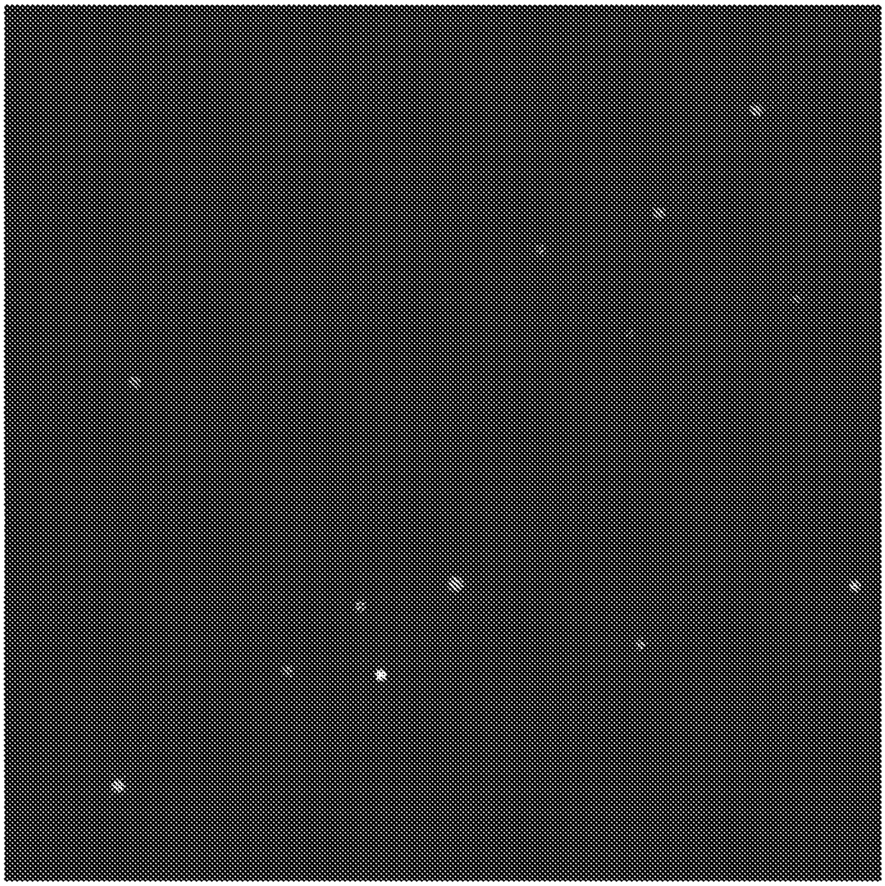
FIG. 5B shows a fluorescence microscope image for a combination of compounds (4) and (8).

First, among compounds (4) to (8), one of green compounds (4), (5) and (6) and one of red compounds (7) and (8) were selected, and each diluted at 100 μmol/L with an assay buffer. The assay buffer has the composition of Tris-HCl buffer solution (pH 9.3) at 100 mmol/L and magnesium chloride at 1.0 mmol/L. Subsequently, a human plasma sample was diluted by 500 times, and added, and the mixture was dispensed into the wells of a microdevice including a multi-well plate. Subsequently, the fluorescence intensity in each well was measured with a fluorescent microscope. FIG. 5A shows a diagram in which the fluorescence intensities in the wells are plotted on a point diagram for all the combinations used in this experiment. FIG. 5B shows a fluorescence microscope image for a combination of compounds (4) and (8).

Example 3

Measurement of Sample from Pancreatic Cancer Patient Using ENPP Probe in Microdevice First, compounds (4) to (8) were each diluted to 100 μmol/L with an assay buffer. The assay buffer has the composition of Tris-HCl buffer solution (pH 9.3) at 100 mmol/L and magnesium chloride at 1.0 mmol/L. Subsequently, plasma samples taken from 31 pancreas cancer patients and 14 healthy persons were each diluted by 500 times, and added, and the mixture was dispensed into the wells of a microdevice including a multi-well plate. Subsequently, the fluorescence intensity in each well was measured with a fluorescent microscope. Data obtained by plotting the fluorescence intensities in the wells on a point diagram was subjected to cluster analysis by fitting to a multivariate normal distribution by variational Bayesian estimation, and the result showed that it was possible to classify the plots into three clusters.

Figure 6A:
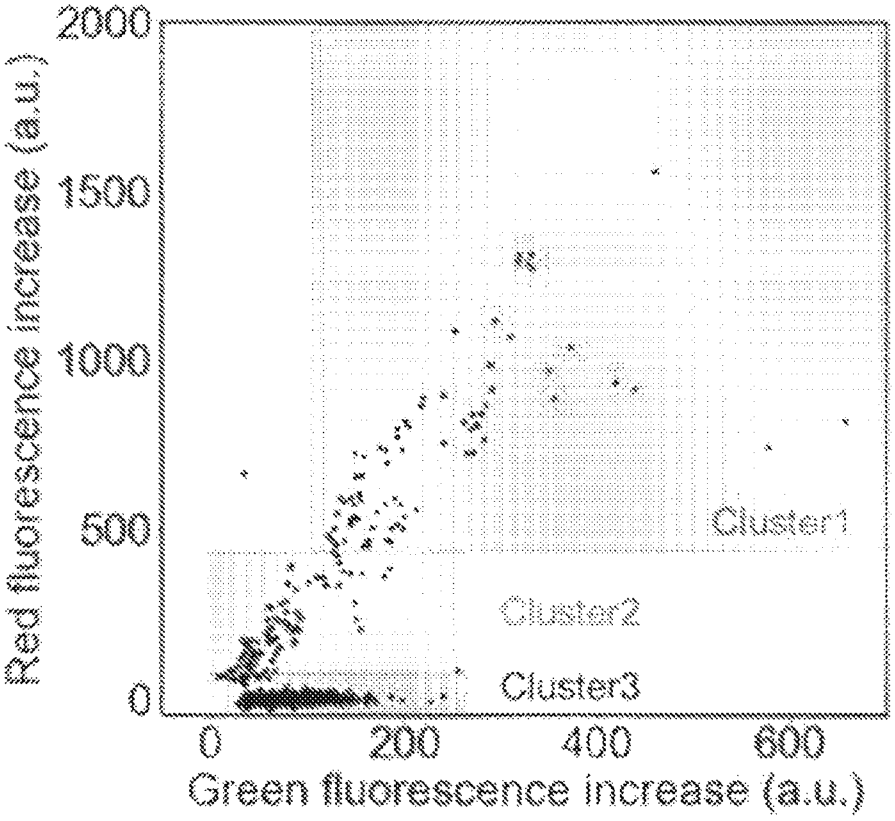
FIG. 6A shows the results of measurement of a pancreas cancer patient sample using an ENPP probe in a microdevice.
Figure 6B:
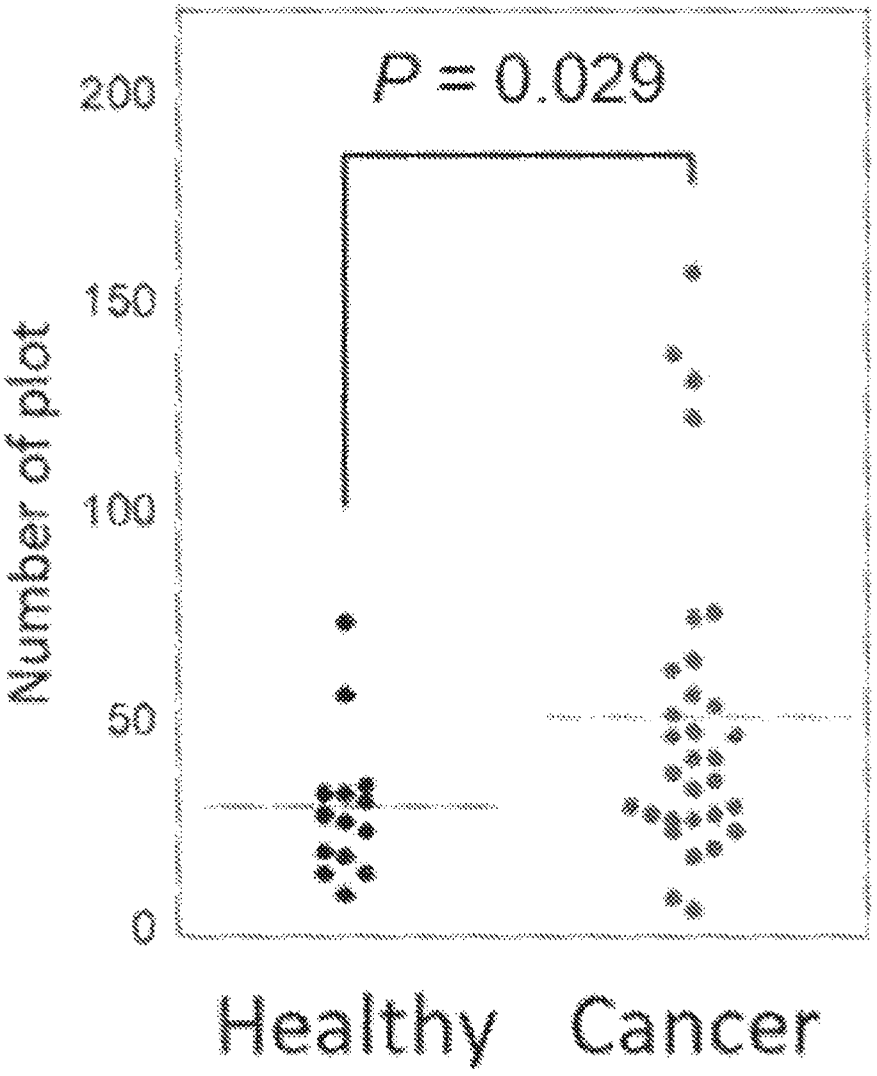
FIG. 6B shows the results of measurement of a pancreas cancer patient sample using an ENPP probe in a microdevice.

An example for one of the samples is shown in FIG. 6A. The number of plots corresponding to cluster 1, i.e. the number of enzymes, was significantly larger for the pancreas cancer patients than for the healthy persons. The results are shown in FIG. 6B.

Example 4

Measurement of Purified Enzyme of ENPP Using ENPP Probe in Microdevice

Figure 7A:
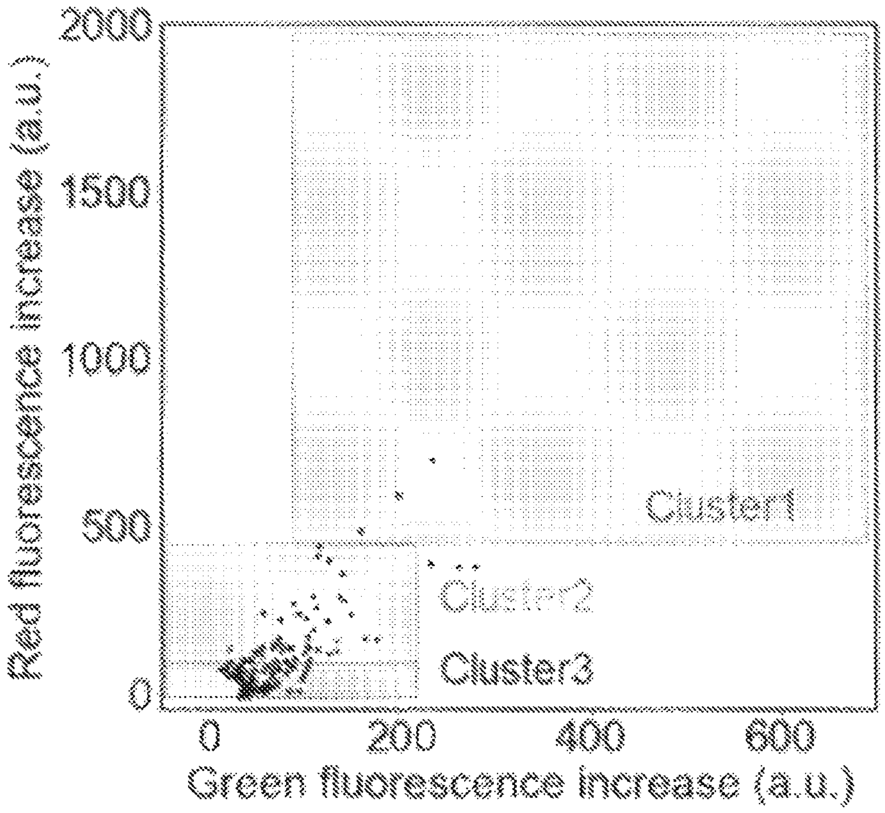
FIG. 7A shows the results of measurement of a purified enzyme of ENPP using an ENPP probe in a microdevice.
Figure 7B:
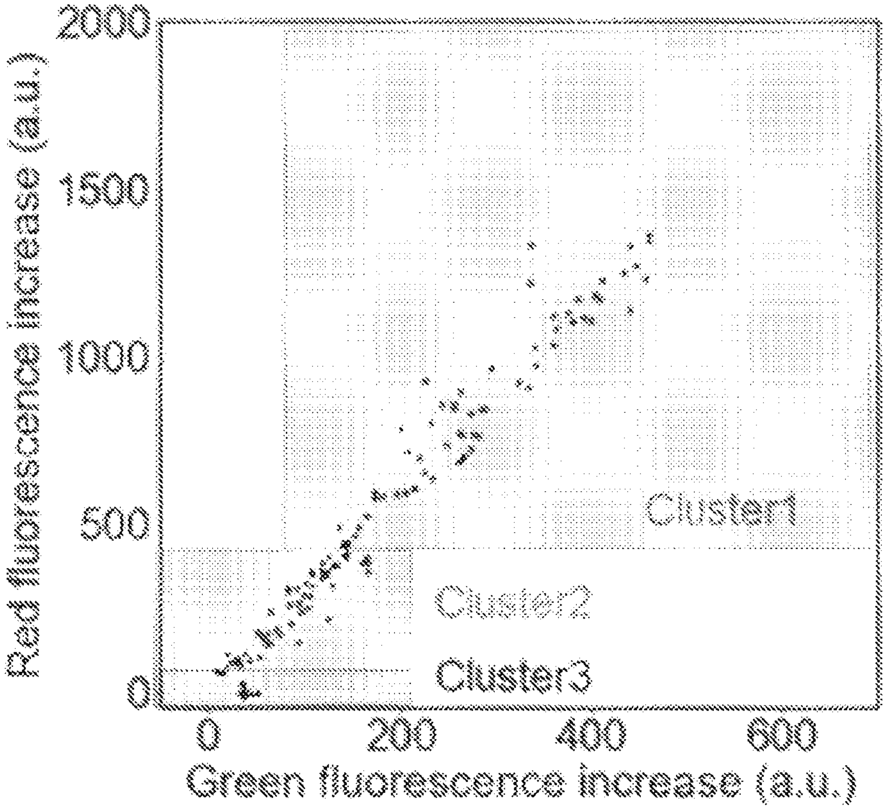
FIG. 7B shows the results of measurement of a purified enzyme of ENPP using an ENPP probe in a microdevice.

First, compounds (4) to (8) were each diluted to 100 μmol/L with an assay buffer. The assay buffer has the composition of Tris-HCl buffer solution (pH 9.3) at 100 mmol/L and magnesium chloride at 1.0 mmol/L. Subsequently, purified enzymes of ENPP1 and ENPP3 were each added, and the mixture was dispensed into the wells of a microdevice including a multi-well plate. Subsequently, the fluorescence intensity in each well was measured with a fluorescent microscope. Data obtained by plotting the fluorescence intensities in the wells on a point diagram was applied to the cluster analysis performed in Example 3. The results thereof are shown in FIG. 7A for ENPP1 and in FIG. 7B for ENPP3. Since only ENPP3 has a plot corresponding to cluster 1, the enzyme that significantly increased in number in pancreas cancer patients in Example 3 may be ENPP3.

Example 5

Measurement of Plasma Sample Using a Plate Reader

Figure 8:
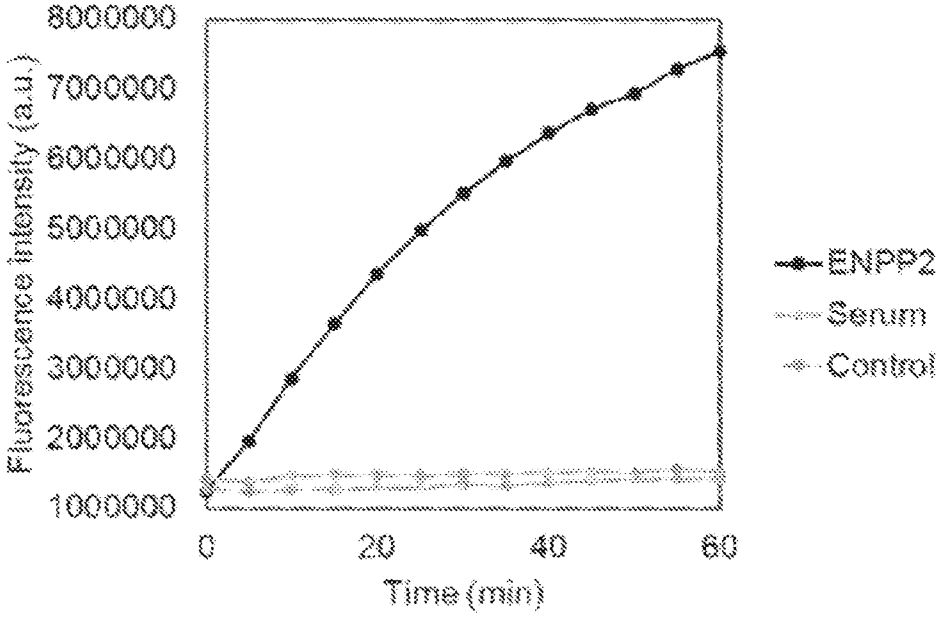
FIG. 8 shows the results of measurement of a plasma sample using a plate reader.

First, compounds (4) was diluted to 10 μmol/L with an assay buffer. The assay buffer has the composition of Tris-HCl buffer solution (pH 8.3), magnesium chloride at 1.0 mmol/L and 0.5% CHAPS. Subsequently, ENPP2 at 25 μg/mL and human serum diluted by 10 times were added, and the mixture was dispensed into a multi-well plate. Subsequently, the fluorescence intensity was measured with a plate reader. The results are as shown in FIG. 8. It is apparent from FIG. 8 that in the multi-well plate, the measured intensity of the activity of ENPP was lower when serum was present than when serum was not present. On the other hand, as described above, the measurement method using a microdevice enabled the activity of ENPP to be adequately measured even in the presence of serum. This indicates that use of a microdevice and a probe suitable for use thereof is advantageous for detecting the activity of ENPP in the blood.

The invention claimed is:

1. A compound of the following general formula (I) or a salt thereof:

(I)

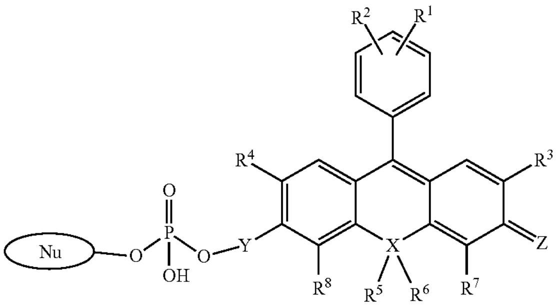

wherein $R^1$ is one or two monovalent substituents present on a benzene ring, which are electron donating groups independently selected from hydroxyl group, alkoxy group having 1 to 10 carbon atoms, amino group and alkylamino group having 1 to 10 carbon atoms;

$R^2$ is one or two monovalent substituents independently selected from the group consisting of a sulfonic acid group and a phosphoric acid group;

$R^3$ and $R^4$ are each independently a hydrogen atom, an alkyl group having 1 to 6 carbon atoms, or a halogen atom;

$R^5$ and $R^6$ are each independently an alkyl group having 1 to 6 carbon atoms, or an aryl group, wherein the aryl group is selected from a monocyclic aromatic group or a condensed aromatic group, wherein the aryl ring may contain one or more ring forming hetero atoms selected from nitrogen atom, oxygen atom or sulfur atom;

$R^7$ and $R^8$ are each independently a hydrogen atom, an alkyl group having 1 to 6 carbon atoms, or a halogen atom;

X is a silicon atom, a phosphorus atom, or a germanium atom;

Z is an oxygen atom or $N^+R^9R^{10}$, where $R^9$ and $R^{10}$ are each independently a hydrogen atom, or an alkyl group having 1 to 10 carbon atoms, $R^9$ and $R^{10}$ are optionally linked together to form a four- to seven-membered heterocyclyl containing a nitrogen atom bonded to $R^9$ and $R^{10}$, and $R^9$ or $R^{10}$, or each of both $R^9$ and $R^{10}$ is optionally linked with $R^3$ or $R^7$ to form a five- to seven-membered heterocyclyl or heteroaryl containing a nitrogen atom bonded to $R^9$ or $R^{10}$, or optionally contains one to three additional hetero atoms selected from the group consisting of an oxygen atom, a nitrogen atom and a sulfur atom as ring forming members, and the heterocyclyl or heteroaryl is optionally substituted with an alkyl having 1 to 6 carbon atoms, an alkenyl having 2 to 6 carbon atoms, an alkynyl having 2 to 6 carbon atoms, an aralkyl group having 6 to 10 carbon atoms, or an alkyl-substituted alkenyl group having 6 to 10 carbon atoms;

Y is a single bond, $—O—(CH_2)_{n1}—$, $—O—(CH_2)_{n2}—Ar_1—$, $—NH—(CH_2)_{n3}—$ or $—NH—(CH_2)_{n4}—Ar_2—$, where n1, n2, n3 and n4 are each independently an integer of 1 to 10, and $Ar_1$ and $Ar_2$ are each independently a substituted or unsubstituted arylene group having 6 to 14 carbon atoms, wherein the substituents are selected from halogen atoms and alkyl groups having 1 to 10 carbon atoms; and Nu is represented by R—S— where R is an organic base selected from the group consisting of a nucleic acid base, $(CH_3)_3N^+—C_2H_4—$, $(CH_3CH_2)_2N—$, and $R'_2N—$, wherein the two R' groups are independently selected from the group consisting of a hydrogen atom, and an alkyl group having 1 to 10 carbon atoms, and S is a sugar selected from ribose, deoxyribose, or a single bond.

2. The compound according to claim 1 or a salt thereof, wherein the nucleic acid base is selected from the group consisting of adenine, thymine, cytosine, guanine and uracil.

3. The compound according to claim 1, wherein $R^1$ is an alkoxy group having 1 to 10 carbon atoms.

4. A fluorescent probe for detecting ENPP, comprising the compound according to claim 1.

5. A test kit for the enzyme activity of ENPP, comprising the compound according to claim 1.

6. A kit comprising the compound according to claim 1 and a plate provided with microwells containing the compound.

7. A method for measuring the enzyme activity of ENPP, comprising bringing ENPP into contact with the compound according to claim 1.

8. The method according to claim 7, wherein the contact is performed in the presence of serum.

9. The kit according to claim 6, comprising two or more types of the fluorescent probes for detecting ENPP which have different reaction points in one well and different fluorescence wavelengths.

* * * * *